United States Patent
Diggett et al.

(10) Patent No.: US 12,131,825 B2
(45) Date of Patent: Oct. 29, 2024

(54) CRITERIA BASED ALARMS COORDINATION BETWEEN A NETWORK OF MEDICAL DEVICES

(71) Applicant: CareFusion 303, Inc., San Diego, CA (US)

(72) Inventors: Lisa Diggett, Overland Park, KS (US); Laura Ann Collins, Collierville, TN (US); Claire Ellen Knight, Arlington, TX (US); Michael K. Workman, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 340 days.

(21) Appl. No.: 17/528,089

(22) Filed: Nov. 16, 2021

(65) Prior Publication Data
US 2022/0165411 A1    May 26, 2022

Related U.S. Application Data

(60) Provisional application No. 63/116,756, filed on Nov. 20, 2020.

(51) Int. Cl.
*G16H 40/67*     (2018.01)
*G16H 40/63*     (2018.01)

(52) U.S. Cl.
CPC ............ *G16H 40/67* (2018.01); *G16H 40/63* (2018.01)

(58) Field of Classification Search
CPC ........ G16H 40/67; G16H 40/63; G16H 10/60; G16H 40/20; A61B 5/002; A61B 5/0205; A61B 5/742; A61B 5/1113
See application file for complete search history.

(56) References Cited

U.S. PATENT DOCUMENTS 5,681,285 A    10/1997  Ford et al.
5,713,856 A    2/1998   Eggers et al.
(Continued)

FOREIGN PATENT DOCUMENTS

| EP | 2623141 A1 | 8/2013 | |
|---|---|---|---|
| EP | 3605550 A1 | 2/2020 | |
| WO | WO-2012152200 A1 * | 11/2012 | ......... G06F 19/3468 |

OTHER PUBLICATIONS

English translation of foreign reference.*
(Continued)

*Primary Examiner* — Jason B Dunham
*Assistant Examiner* — Kimberly A. Sass
(74) *Attorney, Agent, or Firm* — Morgan, Lewis & Bockius LLP

(57) ABSTRACT

The disclosed systems and methods manage more notifications between medical devices. A method includes obtaining information corresponding to a clinician and determining whether the information satisfies coordination criteria. The method includes, in accordance with a determination that the clinician is associated with the first medical device and a second medical device, detecting a first and second notification generated by respective medical devices. The method includes identifying, based on detecting the respective notifications, alert information including medical information for a patient receiving medical treatment from the first and second medical device. The method includes determining, based on the identified information, notification priorities between the respective notifications. The method includes adjusting at least one human perceivable manifestation of the respective notifications based on the determined notification priorities, and presenting adjusted human perceivable manifestations of the respective notifications to the user via one of the first medical device or the second medical device.

20 Claims, 14 Drawing Sheets

(56) References Cited

U.S. PATENT DOCUMENTS

| | | | |
|---|---|---|---|
| 2005/0242928 A1 | 11/2005 | Kirkeby | |
| 2014/0351712 A1* | 11/2014 | Blomquist | G06F 3/0482 715/750 |
| 2021/0012906 A1* | 1/2021 | Muhsin | G16H 40/67 |
| 2021/0059616 A1* | 3/2021 | Abrol | A61B 5/7435 |
| 2021/0151162 A1* | 5/2021 | Tsoukalis | A61M 5/14228 |

OTHER PUBLICATIONS

International Search Report and Written Opinion for Application No. PCT/US2021/060041, dated Mar. 11, 2022, 21 pages.
Qiu et al., "A survey of machine learning for big data processing", EURASIP Journal Advances in Signal Processing, May 28, 2016, Article No. 67 (2016), https://doi.org/10.1186/s13634-016-0355-x.

* cited by examiner

500
(Cont.)

510 (Cont.)

514-a
The coordination criteria includes a remote criterion that is satisfied in accordance with a determination that the current location of the first medical device and the current location of the second medical device are remote, and the method further includes:

514-b
In accordance with a determination that the remote criterion is satisfied, adjusting notification priorities between the first notification and the second notification based on the first medical device and the second medical device being remote to one another

516-a
The coordination criteria includes a patient association criterion that is satisfied in accordance with a determination that the first medical device and the second medical device are associated with the same patient, and the method further comprises:

516-b
In accordance with a determination that the patient association criterion is satisfied, adjust notification priorities between the first notification and the second notification based on the first medical device and the second medical device being associated with the same patient

518
In accordance with a determination that the patient association criterion is not satisfied, adjust notification priorities between the first notification and the second notification based on the first medical device and the second medical device being associated with distinct patients

520
Adjust at least one human perceivable manifestation of the first notification and the second notification based on the determined notification priorities

522
Adjusting the one or more human perceivable manifestations of the first notification and the second notification includes adjusting visual manifestations and/or audible manifestations of the first notification and the second notification

524
Adjusting the one or more human perceivable manifestations of the first notification and the second notification based on the determined notification priorities includes adjusting one or more respective human perceivable manifestations notifications to emphasize higher ranked notifications over lower ranked notifications

Figure 5B

500
(Cont.)

526
Present one or more adjusted human perceivable manifestations of the first notification and one or more adjusted human perceivable manifestations of the second notification to the user via one of the first medical device or the second medical device

528-a
The first medical device and the second medical device are located in a first patient room associated with a first patient, the method further including:

528-b
Detect that the current location of the clinician is in a second patient room associated with a second patient, the second patient room being in a different geographic location than the first patient room;

528-c
Select, based on the determining of the notification priorities, one of the first or second notifications for display at a third medical device located in the second patient room while the clinician is in the second patient room; and

528-d
Present one or more respective adjusted human perceivable manifestations of the selected notification at the third medical device while the clinician is in the second patient room, the first notification and the second notification are not presented at the first medical device and the second medical device while the selected notification is presented at the third medical device

530-a
The one or more human perceivable manifestations of a third notification are received at the third medical device such that the one or more human perceivable manifestations of the third notification are set for presentation by the third medical device during a period of time in which the one or more human perceivable manifestations of the first notification or the one or more human perceivable manifestations of the second notification are generated by the first medical device or the second medical device, respectively, the method further comprising

530-b
overriding the presentation of the one or more human perceivable manifestations of the third notification with the one or more respective adjusted human perceivable manifestations of the selected notification such that the selected notification is presented at the third medication device while the clinician is in the second patient room

Figure 5C 500
(Cont.)

532-a
Determine respective user response times to the adjusted one or more human perceivable manifestations of the first notification and the adjusted one or more human perceivable manifestations of the second notification;

532-b
Identify a respective adjustment to the one or more human perceivable manifestations of the first notification and the one or more human perceivable manifestations of the second notification with the lowest user response time; and

532-c
Adjust subsequent human perceivable manifestations of the first notification and subsequent human perceivable manifestations of the second notification based on the determined notification priorities and adjustments to the one or more human perceivable manifestations with the lowest user response time

534-a
Detecting a third notification generated by a third medical device;

534-b
In accordance with a determination that the clinician identifier is associated with the third medical device, determine the notification priorities between the first notification, the second notification, and the third notification;

534-c
Adjust one or more respective human perceivable manifestations of the first notification, the second notification, and the third notification based on the determined notification priorities; and

534-d
Present the one or more adjusted human perceivable manifestations of the first notification, the one or more adjusted human perceivable manifestations of the second notification, and one or more adjusted human perceivable manifestations of the third notification to the user

536-a
Detect a fourth notification generated by the first or second medical device;

536-b
Determine the notification priorities between the first notification, the second notification, and the fourth notification;

536-c
Adjust the one or more human perceivable manifestations of the first notification, the one or more human perceivable manifestations of the second notification, and one or more human perceivable manifestations of the fourth notification based on the determined notification priorities; and

536-d
Present the one or more adjusted human perceivable manifestations of the first notification, the one or more adjusted human perceivable manifestations of the second notification, and one or more adjusted human perceivable manifestations of the fourth notification to the user.

Figure 5D

CRITERIA BASED ALARMS COORDINATION BETWEEN A NETWORK OF MEDICAL DEVICES

CROSS-REFERENCE TO RELATED APPLICATION(S)

This application claims priority to and is a non-provisional of U.S. Provisional Application Ser. No. 63/116,756, entitled "CRITERIA BASED ALARMS COORDINATION BETWEEN A NETWORK OF MEDICAL DEVICES," filed on Nov. 20, 2020, the entirety of which is incorporated herein by reference.

TECHNICAL FIELD

The present disclosure generally relates alarm management, and more specifically relates to methods and systems for coordinating alarm between medical devices.

BACKGROUND

Existing medical device constantly generate alarms that stress and strain and patients and clinicians. The problem is further exacerbated when multiple medical device are in proximity to each other or within the same building. Further, when multiple medical device are in proximity to each, the different levels of urgency between alarms may not be clearly communicated to a clinician. As such, there is a need to coordinate alarms between medical devices in a way to clearly communicates to clinicians urgencies of the alarms while reducing to generated alarm stress experienced by patients and clinicians.

SUMMARY

According to various implementations, a method for managing one or more notifications between medical devices is provided. The method may include obtaining information corresponding to a clinician. The information includes at least a clinician identifier. The method may include determining whether the information satisfies coordination criteria, the coordination criteria include a device association criterion that is satisfied in accordance with a determination that the clinician identifier is associated with at least a first medical device. The method may include, in accordance with a determination that the clinician identifier is associated with the first medical device and a second medical device thus satisfying at least one coordination criterion, detecting a first notification generated by the first medical device and a second notification generated by the second medical device, the first and second notifications being associated with one or more respective human perceivable manifestations. The method may include identifying, based on detecting the first and second notifications, alert information comprising medical information pertaining to a patient receiving medical treatment from the first medical device and the second medical device. The treatment information pertaining to the medical treatment received from each device, a current location of the first medical device and a current location of the second medical device, and a current location of the clinician. The method include determining, based on the identified information, notification priorities between the first notification and the second notification. The notification priorities include a ranking of the first notification with respect to the second notification based on urgency. The method may include adjusting at least one human perceivable manifestation of the first notification and the second notification based on the determined notification priorities, and presenting one or more adjusted human perceivable manifestations of the first notification and one or more adjusted human perceivable manifestations of the second notification to the user via one of the first medical device or the second medical device.

In some implementations, the first medical device and the second medical device are located in a first patient room associated with a first patient. The method may include detecting that the current location of the clinician is in a second patient room associated with a second patient, the second patient room being in a different geographic location than the first patient room. The method may include selecting, based on the determining of the notification priorities, one of the first or second notifications for display at a third medical device located in the second patient room while the clinician is in the second patient room. The method may further include presenting one or more respective adjusted human perceivable manifestations of the selected notification at the third medical device while the clinician is in the second patient room. The first notification and the second notification are not presented at the first medical device and the second medical device while the selected notification is presented at the third medical device. In some implementations, one or more human perceivable manifestations of a third notification are received at the third medical device such that the one or more human perceivable manifestations of the third notification are set for presentation by the third medical device during a period of time in which the one or more human perceivable manifestations of the first notification or the one or more human perceivable manifestations of the second notification are generated by the first medical device or the second medical device, respectively. The method may further include overriding the presentation of the one or more human perceivable manifestations of the third notification with the one or more respective adjusted human perceivable manifestations of the selected notification such that the selected notification is presented at the third medication device while the clinician is in the second patient room.

In some implementations, the first and/or second medical device is an infusion pump, and the notification priorities between the first notification and the second notification are based, in part, on a type drug, duration of infusion, and/or time remaining for infusion. In some implementations, the notification priorities between the first notification and the second notification are based, in part, on one or more alarm types.

In some implementations, the coordination criteria includes a proximity criterion that is satisfied in accordance with a determination that the current location of the first medical device and the current location of the second medical device are in proximity. The method may further include, in accordance with a determination that the proximity criterion is satisfied, adjusting notification priorities between the first notification and the second notification based on the first medical device and the second medical device being in proximity to one another. In some implementations, the coordination criteria includes a remote criterion that is satisfied in accordance with a determination that the current location of the first medical device and the current location of the second medical device are remote. The method may further include, in accordance with a determination that the remote criterion is satisfied, adjusting notification priorities between the first notification and the second notification based on the first medical device and the second medical device being in proximity to one another. In some implementations, the coordination criteria includes a patient association criterion that is satisfied in accordance with a determination that the first medical device and the second medical device are associated with the same patient. The method may further include, in accordance with a determination that the patient association criterion is satisfied, adjusting notification priorities between the first notification and the second notification based on the first medical device and the second medical device being associated with the same patient. Additionally or alternatively, in some implementations, the method may further include, in accordance with a determination that the patient association criterion is not satisfied, adjusting notification priorities between the first notification and the second notification based on the first medical device and the second medical device being associated with distinct patients.

In some implementations, adjusting the one or more human perceivable manifestations of the first notification and the one or more human perceivable manifestations of the second notification includes adjusting visual manifestations and/or audible manifestations of the first notification and the second notification. In some implementations, adjusting audible manifestations of the first notification and the second notification includes changing the volume, pitch, rate, and/or tone of the first notification and the second notification. In some implementations, adjusting visual manifestations of the first notification and the second notification includes updating a visual color of the first notification and the second notification, or displaying a flash and/or banner for the first notification and the second notification. In some implementations, adjusting the one or more human perceivable manifestations of the first notification and the one or more human perceivable manifestations of the second notification based on the determined notification priorities includes adjusting one or more respective human perceivable manifestations notifications to emphasize higher ranked notifications over lower ranked notifications.

In some implementations, the method includes determining respective user response times to the adjusted one or more human perceivable manifestations of the first notification and the adjusted one or more human perceivable manifestations of the second notification. The method includes identifying a respective adjustment to the one or more human perceivable manifestations of the first notification and the one or more human perceivable manifestations of the second notification with the lowest user response time. The method may further include adjusting subsequent human perceivable manifestations of the first notification and subsequent human perceivable manifestations of the second notification based on the determined notification priorities and adjustments to the one or more human perceivable manifestations with the lowest user response time.

In some implementations, the method may include detecting a third notification generated by a third medical device. The method may include, in accordance with a determination that the clinician identifier is associated with the third medical device, determining the notification priorities between the first notification, the second notification, and the third notification. The method may further include adjusting one or more respective human perceivable manifestations of the first notification, the second notification, and the third notification based on the determined notification priorities, and presenting the one or more adjusted human perceivable manifestations of the first notification, the one or more adjusted human perceivable manifestations of the second notification, and one or more adjusted human perceivable manifestations of the third notification to the user.

In some implementations, the method may include detecting a fourth notification generated by the first or second medical device. The method may include determining the notification priorities between the first notification, the second notification, and the fourth notification. The method may further include adjusting the one or more human perceivable manifestations of the first notification, the one or more human perceivable manifestations of the second notification, and one or more human perceivable manifestations of the fourth notification based on the determined notification priorities, and presenting the one or more adjusted human perceivable manifestations of the first notification, the one or more adjusted human perceivable manifestations of the second notification, and one or more adjusted human perceivable manifestations of the fourth notification to the user.

According to some implementations, a method of managing one or more notifications between medical devices includes detecting a current location of a clinician. The clinician may be currently associated with a first medical device located in a first patient room associated with a first patient, and a second medical device located in a second patient room associated with a second patient, the second patient room being in a different geographic location than the first patient room. The method may include detecting a first notification generated by the first medical device and a second notification generated by the second medical device. The first and second notifications are associated with one or more respective human perceivable manifestations. The method my include identifying, based on detecting the first and second notifications, alert information comprising medical information pertaining to a patient receiving medical treatment from the first medical device and the second medical device. The treatment information pertains to the medical treatment received from each device, a current location of the first medical device and a current location of the second medical device, and the current location of the clinician. The method may include determining, based on the identified information, notification priorities between the first notification and the second notification. The notification priorities include a ranking of the first notification with respect to the second notification based on urgency. The method may include selecting, based on the current location of the clinician in a respective patient room, one of the first or second medical devices to display the first and/or second notifications. The method may further include adjusting at least one human perceivable manifestation of the first notification and the second notification based on the determined notification priorities, and presenting one or more adjusted human perceivable manifestations of the first notification and one or more adjusted human perceivable manifestations of the second notification to the clinician at the selected medical device. A respective notification of a non-selected medical is not generated by the non-selected medical device.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIGS. 5A-5D are flowcharts illustrating a method for managing alarms between patient care devices, according to various aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for coordinating and managing alarms between a network of patient care devices. In particular, the subject technology includes a system and method for providing alarms, alerts, or notifications (all three generally referred to as "notifications") of networked patient care devices to a user (e.g., clinician) at a particular patient care device (e.g., a patient care device which the user is operating). An existing patient care device may constantly generate alarms that can cause stress and strain to patients and clinicians. Further, many patient care devices can be located in proximity to each other, associated with a single patient, and/or associated with a single clinician, which add to the total number of generated alarms. When alarms are generated by networked patient care devices, the system determines a priority between the different alarms provides the alarms to a user (associated with the networked patient care devices) in a way that clearly communicates the different urgency levels between the alarms. More specifically, the system adjusts the alarms generated by the networked patient care devices to highlight urgent alarms to the user. Additionally, the system analyzes user response times and adjusts the alarms generated by the networked patient care devices based, in part, on the user response times. Further, the system and method described herein reduce alarm strain and stress by efficiently and effectively providing alarms to the user.

Figure 1:
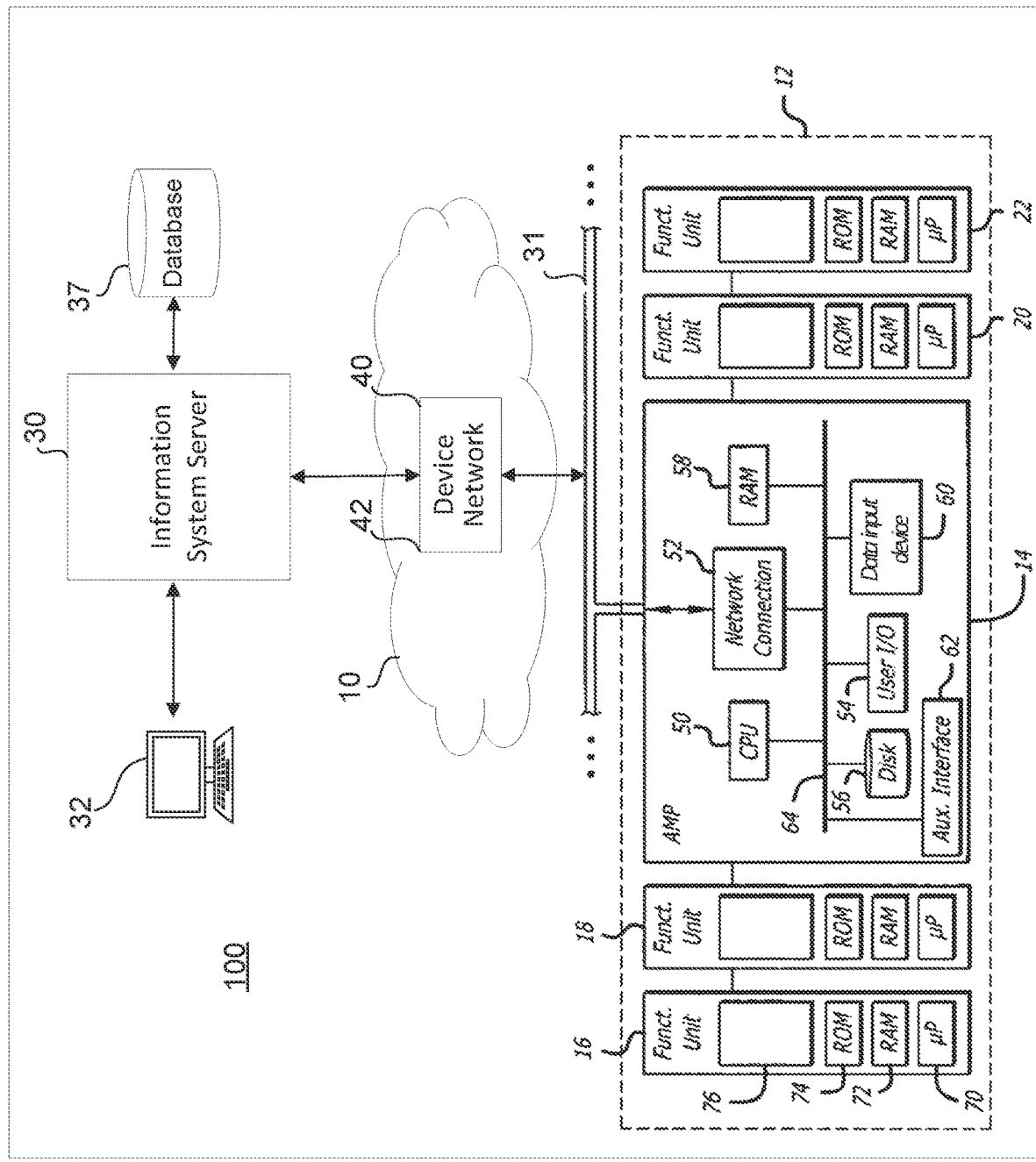
FIG. 1 depicts an example of an institutional patient care system of a healthcare organization, according to various aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term point-of-care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713, 856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. Each mode or personality may include a different set of configuration parameters, or implement a different drug library, as described below. The configuration database may be a database 56 internal to patient care device, or an external database 37. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

In some implementations, the database 56 internal to the PCD 12, and/or the external database 37 includes clinician data. The clinician data includes clinician information, clinician association with one or more PCDs 12 and/or patients, clinician preferences, and/or other relevant clinician information. The clinician information includes a unique identifier for each clinician (or other authorized user) and respective authentication information (e.g., credentials, authentication tokens, passwords, UIDs, authenticated biometric information, etc.) such that the clinician can access PCDs 12 they are associated with. The clinician preferences include configurations for manifestation of notifications, such as clinician specific visual manifestations of notifications (e.g., colors, flashes, font (e.g., size and/or style), banners, backgrounds, background effects, overlays, and/or other visual effects), clinician specific audio manifestations of notifications (e.g., volume, tone, pitch, patterns, and/or rate), other clinician specific human perceivable manifestations of notifications (e.g., haptic feedback, vibrations, etc.), and/or accommodations for clinician disabilities and/or impairments (e.g., color blindness, hearing loss, deafness, blindness, etc.). In some implementations, the clinician data includes clinician interaction with a PCD 12. A non-exhaustive list of clinician interaction with a PCD 12 includes client response times to notification manifestations (or lack thereof), inputs provided to the PCDs 12 (and/or functional models 16, 18, 20, 22), current and past programming configurations, interactions with other networked PCDs 12, etc. In some implementations, the clinician interaction with a PCD 12 is used to determine one or more manifestations of notifications for the clinician as well as adjustments to the manifestations.

In some implementations, the database 56 internal to the PCD 12, and/or the external database 37 includes patient specific configuration data for the manifestations of notifications. The patient specific configurations include patient specific visual manifestation of notifications, patient specific audio manifestations of notifications, other patient specific human perceivable manifestations of notifications, and/or accommodations for patient conditions or illnesses (e.g., light sensitivity, audio sensitivity, sleep patterns, etc.). In particular, the patient specific configurations can define, for a patient, manifestations of notifications and adjustments for the manifestations of notifications such that a clinician can easily identify the patient and/or to assign a patient with manifestations of notifications that cause the least amount stress or strain to the patient. For example, a patient with light sensitivity may not have manifestations of notifications with continuous flashes or bright lights.

In some implementations, the database 56 internal to the PCD 12, and/or the external database 37 includes PCD 12 specific data for the manifestations of notifications. The PCD 12 specific data includes information corresponding to one or more components (e.g., speakers, displays, illuminating devices (e.g., LEDs), haptic devices, etc.) of the PCD 12 and/or manifestations of the notifications that the PCD 12 is capable of presenting. For example, the PCD 12 specific data can indicate that the PCD 12 does not have any speakers and therefore cannot present audio manifestations of the notification. Alternatively, the PCD 12 specific data can indicate that the PCD 12 is in communication with at least one functional model 16, 18, 20, 22 that includes a speaker and the PCD 12 can be configured to present the audio manifestations of the notification via the functional model's speaker. In this way, the PCD 12 is able to adjust the manifestations of the notifications within the limits of its configuration. In some implementations, the PCD 12 specific data includes time and date information as well as information on other environmental conditions (e.g., surrounding sounds, current lighting, temperature, etc.), which are used to determine one or more manifestations of the notifications and adjustments thereof (e.g., adjustments to manifestations for night, early morning, loud rooms, etc.). In some implementations, the PCD 12 specific data includes location data, which is used to determine one or more manifestations of the notifications and adjustments thereof. For example, the PCD 12 can use its location data in conjunction with the location data of other PCDs 12 to determine one or more adjustments to the manifestations of the notifications such that additional manifestations of notifications do not significantly increase the generated alarm stress and strain.

In some implementations, the PCD 12, and/or the external database 37 includes manifestation data for configuring the notifications. The manifestation data includes visual and/or audio adjustments for manifestations of notifications, which are configured to comply with the standards set for in IEC 60601.

A controller 14 of patient care device 12 also has access to a drug library. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. "Drug Library Profiles" may be established in which medications (e.g., drugs), concentrations, and other pumping parameters are set particular to that care area—such as, for example, an ICU (intensive care unit) profile, a pediatric profile, a neonatal profile and others. Data sets of medications allowed for use and configurations of pumping parameters including limitations for that use may be available for each drug library profile. As such, drug library profiles may, although not necessarily, correspond to different patient care areas of the hospital. Thus a controller 14 located in a pediatric ward, for example, may utilize a pediatric drug library profile that includes sets of allowed medications, pumping parameters, and pumping limitations that are specific to patients classified as pediatric or located in a pediatric ward. Similarly, a controller 14 located in an ICU may utilize an ICU drug library profile that includes a different set of allowed medications, pumping parameters, and pumping limitations that are specific to patients located in an intensive care environment and other patients requiring intensive care.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2:
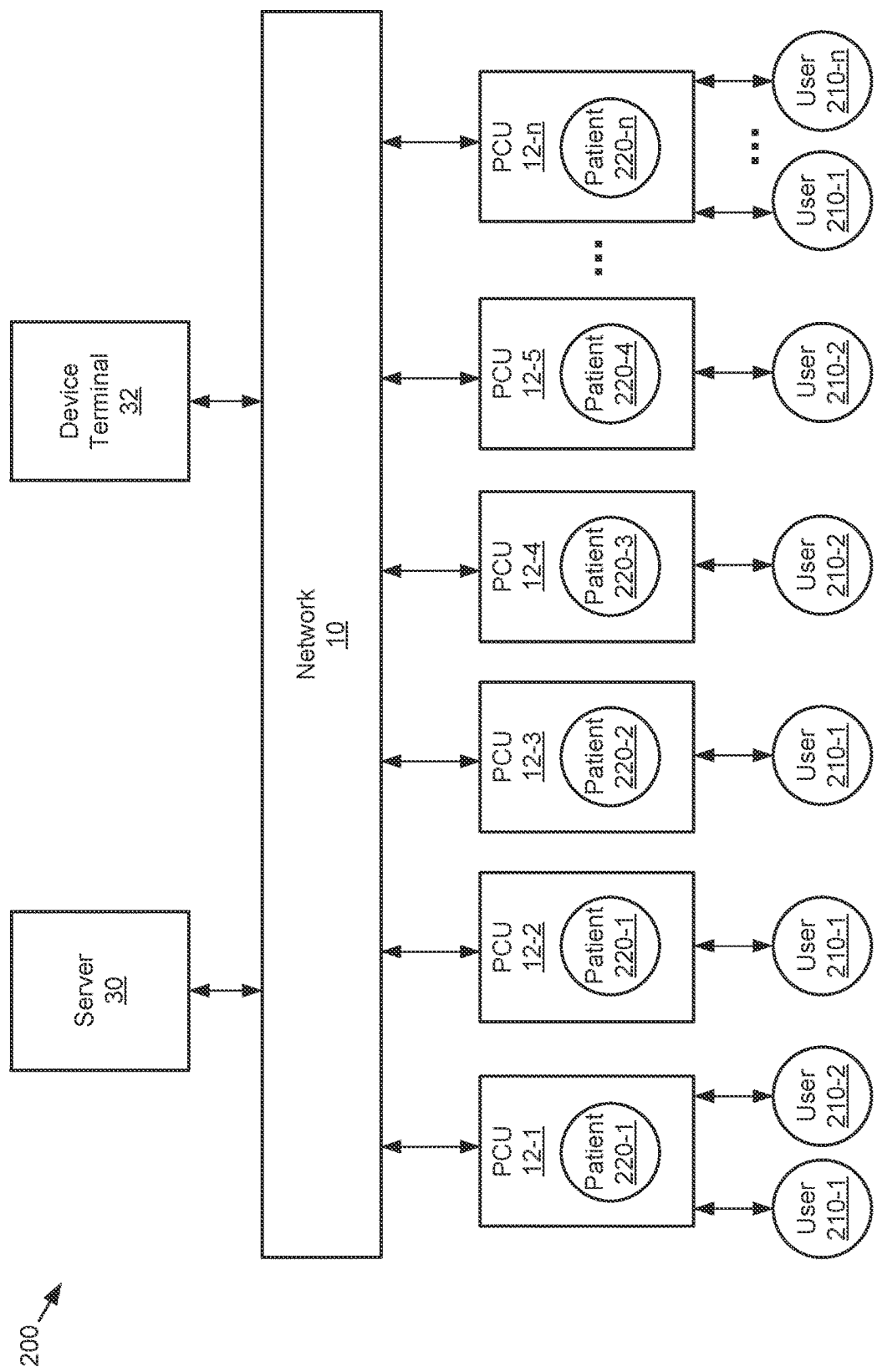
FIG. 2 illustrates an overview of a network of patient care devices, according to various aspects of the subject technology.

FIG. 2 illustrates a system overview of networked PCDs, in accordance with some implementations. The system 200 includes a network 10, server 30, one or more device terminals 32, and one or more PCDs 12. The one or more PCDs 12 may be associated with one or more users 210 (e.g., clinicians) and/or patients 220. For purposes of this disclosure, a user 210 is a clinician or other authorized user of a PCD 12 or other medical device, and a patient 220 is an individual using or otherwise receiving medical treatment from a PCD 12 or other medical device. The server 30, one or more device terminals 32, and/or one or more PCDs 12 (generally referred to as "communicatively coupled devices") are communicatively coupled via network 10, which allows the communicatively coupled devices to coordinate and manage notifications between the network of patient care devices.

To coordinate and manage notifications between the network of patient care devices, the server 30, device terminals 32, and/or PCDs 12, either alone or in combination, identify one or more PCDs 12 associated with a user 210 and/or patient 220. For example, in some implementations, the server 30 identifies that a first user 210-1 is associated with a first, second, third, and nth PCD (12-1, 12-2, 12-3, and 12-*n*; where n is an integer greater than zero); a second user 210-2 is associated with the first, fourth, and fifth PCD (12-1, 12-4, and 12-5); and nth user 210-*n* (where n is an integer greater than zero) is associated with the nth PCD 12-*n*. Continuing the example, in some implementations, the server 30 identifies that a first patient 220-1 is associated with the first PCD 12-1 and the second PCD 12-2; a second patient 220-2 is associated with the third PCD 12-3; a third patient 220-3 is associated with the fourth PCD 12-4; a fourth patient 220-4 is associated with the fifth PCD 12-5; and an nth patient 220-*n* (where n is an integer greater than zero) is associated with the nth PCD 12-*n*. Additionally or alternatively, the communicated coupled devices, either alone or in combination, identify users 210 associated with patients 220, and vice versa.

As shown in system overview 200, in some implementations, the one or more PCDs 12 are associated with the same patient (e.g., the first patient 220-1 is associated with the first PCD 12-1 and the second PCD 12-2). Alternatively or additionally, in some implementations, the one or more PCDs 12 are associated with distinct patients (e.g., the third PCD-12-3 is associated with the second patient 220-2 and the fourth PCD 12-4 is associated with the third patient 220-3). Similarly, in some implementations, the one or more PCDs 12 are associated with the same or distinct users 210. For example, both the first user 210-1 and second user 210-2 are associated with the first PCD 12-1; however, the third PCD-12-3 is associated with the first user 210-1 and the fourth PCD 12-4 is associated with the second user 210-2.

As discussed in further detail below, the communicated coupled devices detect one or more notifications generated by the one or more PCDs 12 and determine notification priorities between the respective notifications generated by the one or more one or more PCDs 12. More specifically, in some implementations, the notification priorities identify a level of urgency between the different detected notifications. In some implementations, the notification priorities include a ranking of the notifications where urgent and/or critical notifications are ranked higher than routine or non-critical notifications. The communicated coupled devices adjust respective human perceivable manifestations of the notifications generated by the one or more PCDs 12 based on the determined notification priorities, and present the adjusted human perceivable manifestations of the notifications to the corresponding user 210. In this way, a user 210 is provided with the different notifications generated by the PCDs 12 with which she is associated, and the notifications clearly communicate their corresponding level of urgency.

Figure 3:
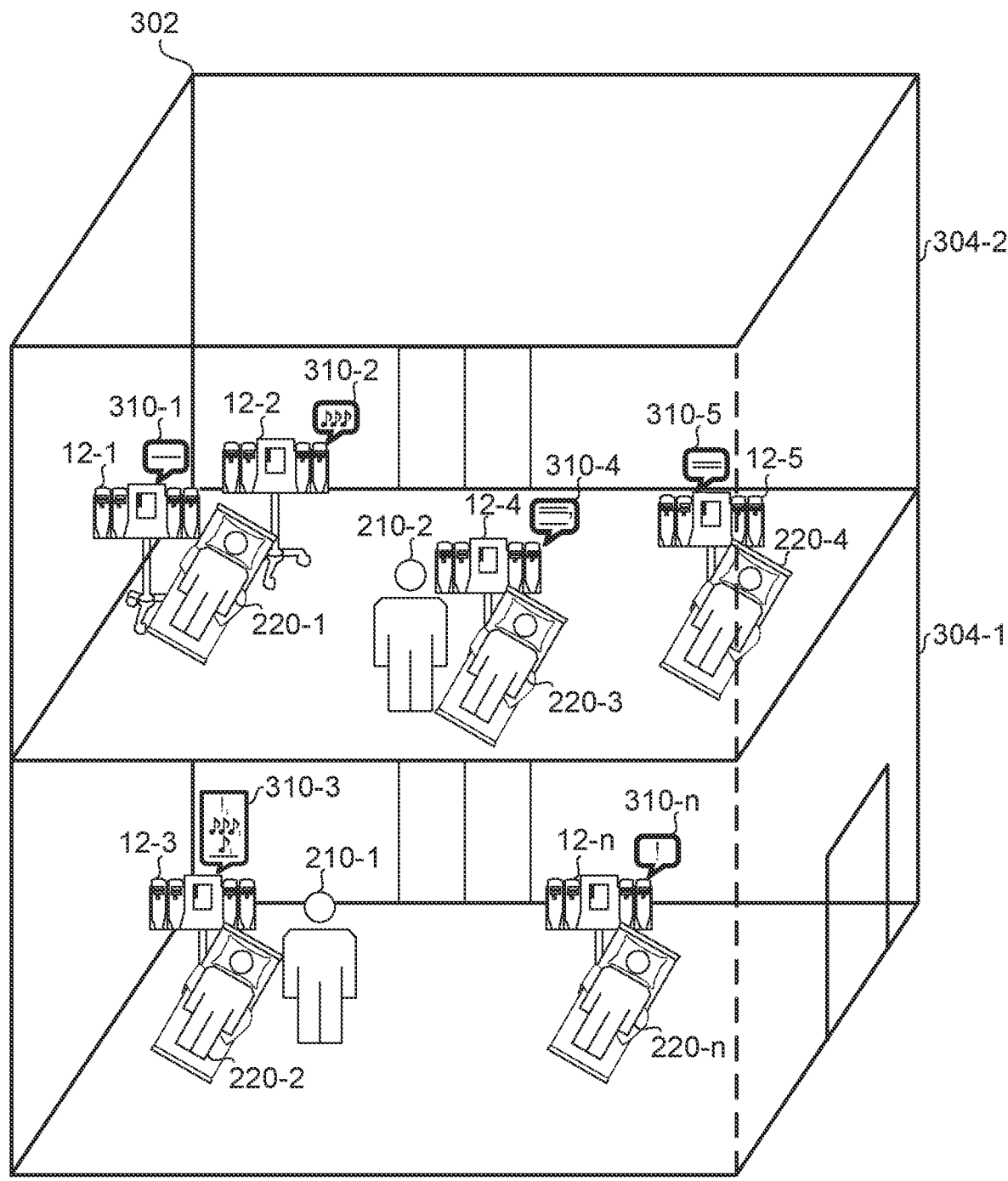
FIG. 3 illustrates coordinated notifications between patient care devices, according to various aspects of the subject technology.

FIG. 3 illustrates coordinated notifications between PCDs, according to various aspects of the subject technology. An operational overview 300 includes a building 302 with one or more floors (e.g., first floor 304-1 and second floor 304-2), one or more PCDs 12, one or more users 210, one or more patients 220, and/or one or more human perceivable manifestations of the notifications 310. As described above in FIG. 2, in some implementations, the users 210 and/or patients 220 are associated with the one or more PCDs 12. For simplicity, in operational overview 300, a first user 210-1, second user 210-2, and patients (220-1 through 220-*n*) are associated with the one or more PCDs (12-1 through 12-*n*) as described in FIG. 2. For example, the first user 210-1 is associated with the first, second, third, and nth PCD (12-1, 12-2, 12-3, and 12-*n*) and the second user 210-2 is associated with the first, fourth, and fifth PCD (12-1, 12-4, and 12-5).

A PCD 12 (and/or other communicatively coupled device) identifies one or more users 210 and/or patients 220 associated with the PCD 12, other PCDs 12, and/or other medical devices. For example, the fourth PCD 12-4 may identify that the second user 210-2 is associated with the first, fourth, and fifth PCD (12-1, 12-4, and 12-5). As another example, the second PCD 12-2 may identify that the first patient 220-1 is associated with the first PCD 12-1 and the second PCD 12-2. In some implementations, the PCD 12 identifies its physical location, the physical location of other PCDs 12 and/or medical devices, and/or its relative position with respect to other PCDs 12 and/or other medical devices. In some implementations, the one or more PCDs 12 are determined to be in proximity to one another and/or other medical devices. Proximity, for purposes of this disclosure, means that the one or more PCDs 12 are on the same floor, in the same room, and/or adjacent to one another. For example, in operational view 300, the first, second, fourth, and fifth PCDs (12-1, 12-2, 12-4, and 12-5) are proximate to one or another. Alternatively or additionally, in some implementations, the one or more PCDs 12 are remotely located. Remotely located PCDs, for purposes of this disclosure, are PCDs 12 (and/or other medical devices) on different floors, in different wings of a building, and/or in different buildings. For instance, in operational view 300, the first PCD 12-1 is remotely located from the third PCD 12-3, and vice versa.

The PCD 12 detects one or more human perceivable manifestations of the notifications 310 generated by one or more PCDs 12, other PCDs 12, and/or other medical devices. For example, in operational view 300, the third PCD 12-3 detects one or more human perceivable manifestations of a first notification 310-1 generated by the first PCD 12-1, one or more human perceivable manifestations of a second notification 310-2 generated by the first PCD 12-2, and one or more human perceivable manifestations of an nth notification 310-n generated by the nth PCD 12-n. It should be noted that the third PCD 12-3 may generate its own notification e.g., one or more human perceivable manifestations of a third notification 310-3, illustrated by a single music chord) along with the identified notifications. Similarly, a PCD 12 may detect one or more one or more human perceivable manifestations of notifications 310 generated by one or more PCDs 12 without generating their own notification (e.g., fourth PCD 12-4, discussed below). Additionally, each PCD 12 can generate more than one notification, and the one or more generated notifications can have the same or different urgency levels.

The PCD 12 further determines notification priorities between the detected notifications generated by the one or more PCDs 12. For example, continuing the above example, the third PCD 12-3 can determine notification priorities between the one or more human perceivable manifestations of the first notification 310-1, the one or more human perceivable manifestations of the second notification 310-2, the one or more human perceivable manifestations of the nth notification 310-n and/or its own notification (e.g., the one or more human perceivable manifestations of the third notification 310-3, if generated). In some implementations, the notification priorities include rankings for the respective notifications based on urgency. For example, urgent notifications will be ranked higher than intermediate notifications, while routine and/or informational notifications will lower ranked than urgent and intermediate notifications. For illustrative purposes, in operational overview 300, the respective priorities are as follow: the one or more human perceivable manifestations of the first notification 310-1 includes a routine and/or information notification (illustrated by a single line); the one or more human perceivable manifestations of the second notification 310-2 includes an intermediate or urgent notification (illustrated by three music chords); the one or more human perceivable manifestations of the third notification 310-3 includes a routine and/or informational notification (illustrated by a single music chord) and, as discussed below, further includes the one or more human perceivable manifestations of the first notification 310-1, the one or more human perceivable manifestations of the second notification 310-2, and the one or more human perceivable manifestations of the nth notification 310-n; one or more human perceivable manifestations of a fifth notification 310-5 includes an intermediate or urgent notification (illustrated by two lines), and the one or more human perceivable manifestations of an nth notification includes an urgent notification (illustrated by "!" representative a haptic feedback or other perceivable manifestation). A PCD 12 does not need to generate its own notification to generate one or more notifications corresponding to other PCDs 12. For example, one or more human perceivable manifestations of a fourth notification 310-4 do not include notifications generated by the fourth PCD 12-4, but include the one or more human perceivable manifestations of the first notification 310-1 and the one or more human perceivable manifestations of the fifth notification 310-5 (i.e., notifications from other PCDs 12 associated with the second user 210-2). For simplicity, the one or more PCDs 12 illustrated in FIG. 3 generate either a visual or audible notification; however, a PCD 12 can generate one or more notifications that include both visual, audible, and/or other human perceivable manifestations.

In some implementations, the PCD 12 includes (or operates) as an infusion pump, and the determined notification priorities between the detected notifications generated by the one or more PCDs 12 are based, in part, on a type drug being infused, duration of infusion, and/or time remaining for infusion. Alternatively or additionally, in some implementations, the determined notification priorities between the detected notifications generated by the one or more PCDs 12 are based, in part, on one or more alarm types. In some implementations, the one or more alarm types include general information useful to a user 210 and/or a type of fault detected by the PCD 12 and/or any auxiliary medical device coupled to the PCD 12. For example, for a PCD 12 operating as an infusion pump, an alarm type can indicate a flow error, occlusion (and its general location), infusion has ended or is near ending, callback, and/or any other type of general information or detected fault that is relevant to the user 210.

The PCD 12 adjusts one or more human perceivable manifestations of the notifications generated by the one or more PCDs 12 based on the determined notification priorities, and presents the one or more adjusted human perceivable manifestations of notifications to a user 210. In particular, the PCD 12 may adjust one or more human perceivable manifestations of the generated notifications to make urgent (or higher ranked) notifications more prominent than less urgent (or lower ranked) notifications. For example, the third PCD 12-3 may adjust the one or more human perceivable manifestations of the first notification 310-1, the one or more human perceivable manifestations of the second notification 310-2, the one or more human perceivable manifestations of the nth notification 310-n, and/or its own notification (e.g., the one or more human perceivable manifestations of the third notification 310-3, if generated) based on their respective notification priorities such that the one or more human perceivable manifestations of the nth notification 310-n are more prominent than the one or more human perceivable manifestations of the second notification 310-2, the one or more human perceivable manifestations of the second notification 310-2 are more prominent than the one or more human perceivable manifestations of the third notification 310-3, the one or more human perceivable manifestations of the third notification 310-3 is more prominent and/or equally as prominent as the one or more human perceivable manifestations of the first notification 310-1. As shown in operational overview 300, the third PCD 12-3 is able to present the one or more adjusted human perceivable manifestations of the notifications to the first user 210-1 based on the determined notification priorities. As another example, the fourth PCD 12-4 may adjust the one or more human perceivable manifestations of the first notification 310-1 and the one or more human perceivable manifestations of the fifth notification 310-5 such that the one or more human perceivable manifestations of the fifth notification 310-5 are more prominent that the one or more human perceivable manifestations of the first notification 310-1, and present both the fifth notification 310-5 and the first notification 310-1 via a fourth notification 310-4 even though the fourth PCD 12-4 did not generate its own notification.

The one or more human perceivable manifestations of the notifications 310 can be audible manifestations, visual manifestations, and/or other human perceivable manifestation (as discussed below with respect to FIG. 4). In some implementations, the adjusted one or more human perceivable manifestations of the notifications are made more prominent by adjusting the visual manifestations and/or audible manifestations of the one or more generated notifications. In some implementations, adjusting audible manifestations includes changing the volume, pitch, rate, and/or tone of the one or more generated notification. In some implementations, adjusting visual manifestations of the one or more generated notifications includes updating a visual color of the first notification and the second notification, or displaying a flash and/or banner of the one or more generated notification 310. The different adjustments to the one or more human perceivable manifestations of the generated notifications are discussed below with respect to FIG. 4.

The one or more human perceivable manifestations of the notifications 310 are presented at a PCD 12 that has a user's 210 attention (i.e., that the user 210 has accessed, is logged into, or determined to be focused on (e.g., based on the interactions with the PCD 12)). More specifically, a PCD 12 currently being operated by a user 210 will provides its own human perceivable manifestations of notifications and/or one or more human perceivable manifestations of notifications generated by other the PCDs 12 associated with the user 210 (after adjusting the human perceivable manifestations of the notifications based on the determined notification priorities). A user 210 can access the PCD 12 in various ways, such as entering their login credentials into the PCDs, using a proximity and/or vicinity cards, and/or other methods known in the art. In some implementations, a PCD 12 may provide its own human perceivable manifestations of the notifications until a user 210 accesses the PCD 12, at which point the PCD 12 will provide its own human perceivable manifestations of the notifications and/or one or more human perceivable manifestations of the notifications generated by other PCDs 12 associated with the user 210 (after adjusting the human perceivable manifestations of the notifications based on the determined notification priorities). In this way, a PCD 12 can continue to provide its own human perceivable manifestations of the notification to passing users 210 and provide human perceivable manifestations of the notifications generated by other PCDs 12 after a user 210 has been authenticated.

In some implementations, the PCD 12 determines user response times to the adjusted human perceivable manifestations of the notifications and identifies adjustments (to the human perceivable manifestations of the notifications) with the lowest user response time. In some implementations, the PCD 12 adjusts subsequent (or future) human perceivable manifestations of the notifications based on the determined notification priorities and the identified adjustments with the lowest user response time. In other words, the PCD 12 learns, over time, the response times for different adjustments (to human perceivable manifestations of the notifications), and can dynamically selects adjustments to the human perceivable manifestations of the notifications based on the response time such that urgent notifications receive the quickest response. For example, if the PCD 12 determines that the first user 210 responds to audible manifestations of the notifications before visual manifestations of the notifications, the PCD 12 adjusts urgent notifications with audible manifestations (along with any visual manifestations required by IEC 60601). As another example, if the PCD determines that the second user 210-1 responds to flashing lights before brightly colored banners, the PCD 12 adjusts urgent notifications with flashing lights (along with any audible cues required by IEC 60601). Similarly, if the PCD determines that the second user 210-1 responds to high pitch alarms before frequently sounded tones, the PCD 12 adjusts urgent notifications to include high pitch alarms.

In some implementations, any PCD 12 associated with a user 210 can present to the user 210 generated notifications corresponding to a patient 220 and/or other PCDs 12 associated with the user 210. For instance, the first user 210 can receive human perceivable manifestations of the notifications from the first, second, third, and/or nth PCDs (12-1, 12-2, 12-3, and 12-*n*) at any of the first, second, third, and/or nth PCDs (12-1, 12-2, 12-3, and 12-*n*). Similarly, the human perceivable manifestations of the notifications presented to the user 210 can correspond to the same or different patients. For example, a second user 210-2 can receive human perceivable notifications corresponding to the first, third, and/or fourth patients (220-1, 220-3, and 220-4) from the first, fourth, and/or fifth PCDs (12-1, 12-4, and 12-5).

In some implementations, while a user 210 is accessing (or operating) a first PCD 12, a second PCD 12 that is associate with the user 210 may generate a notification 310. In some implementations, the notification generated to the second PCD 12 can be provided to the user 210 via the first. PCD 12. If the second PCD 12 is in proximity to the first PCD 12, the user 210 can acknowledge and suppress for a predetermined period of time (e.g., at least 30 sec) the notification generated by the second PCD 12. For example, as illustrated in operational view 300, the second user 210-2 is responding to the fourth notification 310-4 generated by the fourth PCD 12-4, and, while the second user 210-2 is operating the fourth notification 310-4, the fifth notification 310-5 is generated (or is about to be generated) by the fifth PCD 12-5. While the second user 210-2 is accessing (or operating) the fourth PCD 12-4, and because the second user 210-2 is also associated with the fifth PCD 12-5 and in proximity to the fifth PCD 12-5, the fifth notification 310-5 generated (or about to be generated) by the fifth PCD 12-5 may be acknowledged by the second user 210-2 and suppressed for a predetermined period of time at the fourth PCD-4. More specifically, a user 210 is accessing a first PCD 12 can remotely acknowledged and/or suppressed (for a predetermined period of time) notifications 310 generated by other PCDs 12 if the user 210 is in proximity to (and associated with) the other PCDs 12.

Although the examples provided above are performed by the PCD 12, those of skill in the art would appreciate that the above examples can also be performed by the server 30 and/or device terminal 32.

Figure 4:
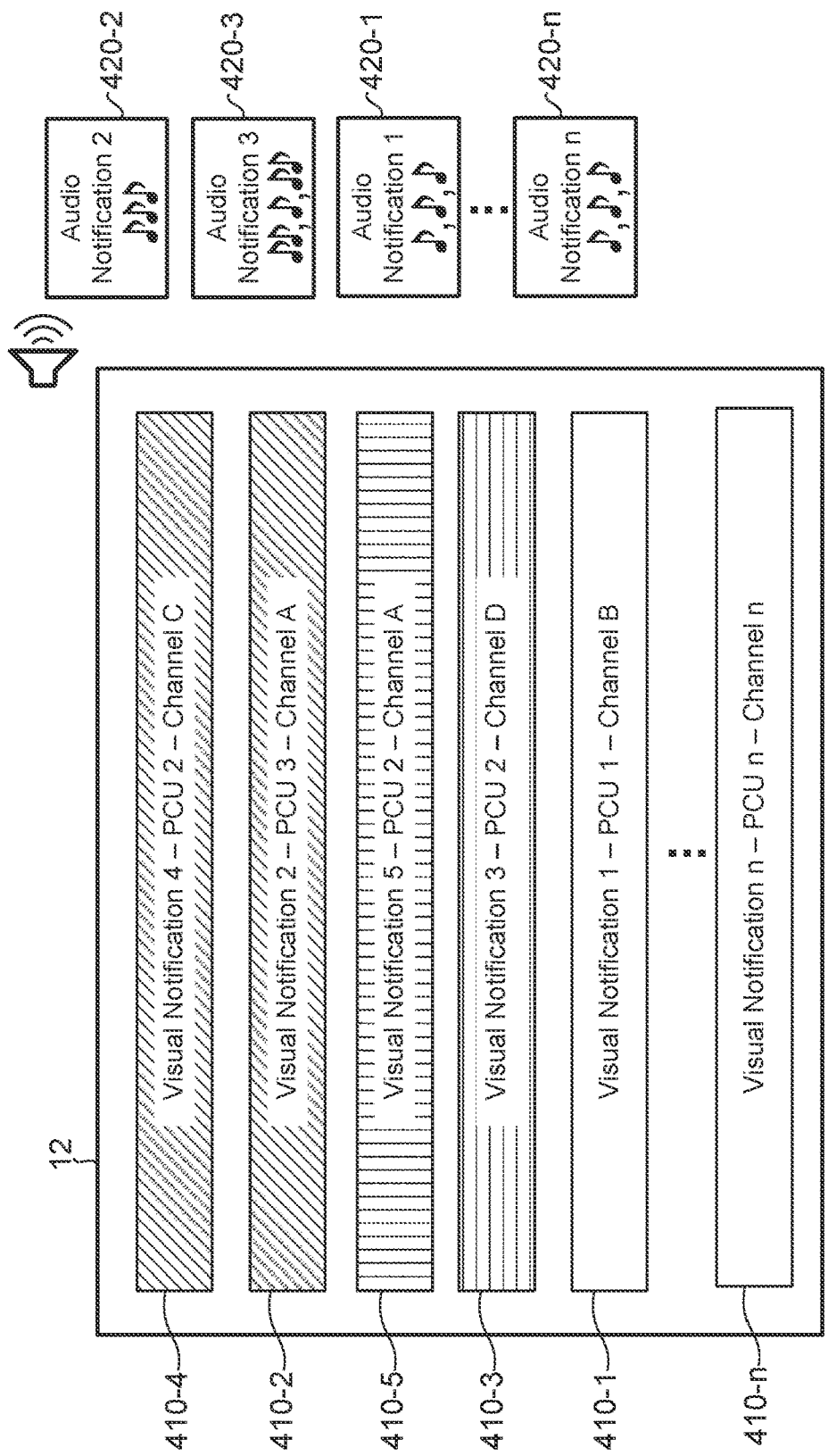
FIG. 4 illustrates prioritized notifications generated by a network of patient care devices, according to various aspects of the subject technology.

FIG. 4 illustrates prioritized notifications generated by a network of PCDs, according to various aspects of the subject technology. In notification overview 400, notifications generated by the network of PCDs are displayed at a PCD 12. In some implementations, the notifications provided by the PCD 12 are positioned and/or ordered such that a user 210 (FIG. 2) is presented with human perceivable manifestations of the notifications based on determined notification priorities (i.e., higher ranked notifications are made more prominent than lower ranked notifications) as described above in FIG. 3. For example, an urgent notification may be displayed before and/or above a less urgent and/or routine notification. Similarly, an urgent notification may be audible before and/or made distinguishable from a less urgent and/or routine notification. In some implementations, the notifications include information corresponding to the PCD 12 that generated the notification, one or more functional modules 16, 18, 20, 22 (FIG. 1) of the PCD 12 that needs attention, a type of alarm and/or urgency level, a patient 220 for whom the notification was generated, and/or general information corresponding to the notification (e.g., end of infusion, time remaining, etc.).

In some implementations, the human perceivable manifestations of notifications provided by the PCD 12 are visually and/or audibly adjusted manifestations of notifications (e.g., visually adjusted manifestation of the notifications 410 and/or audibly adjusted manifestations of the notifications 420). In some implementations, the PCD 12 visually and/or audibly adjusts manifestations of the notifications based on determined notification priorities (i.e., higher ranked notifications are made more prominent than lower ranked notifications). The visually adjusted manifestations of the notifications 410 and/or audibly adjusted manifestations of the notifications 420 are provided to the user 210 associated with the PCD 12 (and/or associated with the other networked PCDs 12). In this way, the user 210 is provided one or more notifications generated by the networked PCDs (associated with the user 210) at a single PCD 12 (e.g., a PCD 12 that the user 210 is currently operating). The visually adjusted manifestations of the notifications 410 and/or audibly adjusted manifestations of the notifications 420 are provided to the user 210 in a way that highlights and/or emphasizes urgent notifications over less urgent and/or routine notifications. More specifically, in some implementations, the PCD 12 visually and/or audibly adjusts the one or more manifestations of the notifications such that the urgency of one or more notifications is clearly communicated to the user 210.

In some implementations, the visually adjusted manifestations of the notifications 410 and/or the audibly adjusted manifestations of the notifications 420 are generated by the same PCD 12 and/or distinct PCDs 12 of the network 10. In some implementations, the visually adjusted manifestations of the notifications 410 and/or the audibly adjusted manifestations of the notifications 420 correspond to the same patient (e.g., a patient 220 associated with multiple PCDs 12). Alternatively or additionally, in some implementations the visually adjusted manifestations of the notifications 410 and/or the audibly adjusted manifestations of the notifications 420 correspond to distinct patients (e.g., patients 220 associated with different PCDs 12, but associated with the same user 210).

In notification overview 400, the PCD 12 provides a first, second, third, fourth, fifth, and nth visually adjusted manifestations of the notifications 410-1, 410-2, 410-3, 410-4, 410-5, and 410-n (where n is an integer greater than zero). The fourth and second visually adjusted manifestations of the notifications (410-2 and 410-4) are determined to be more urgent than (and are therefore displayed above) the first, third, fifth, and nth visually adjusted manifestations of the notifications (410-1, 410-3, 410-5, and 410-n). The fifth visually adjusted manifestations of the notification 410-5 is determined more urgent than the first, third, and nth visually adjusted manifestations of the notifications (410-1, 410-3, and 410-n) and, as such, displayed above them. Similarly, the third visually adjusted manifestations of the notification 410-3 is determined more urgent than, and displayed above, the first and nth visually adjusted manifestations of the notifications (410-1 and 410-n). The ordering of the notifications allows the user 210 to easily focus on the more urgent notifications before addressing less urgent notifications.

In some implementations, visually adjusting manifestations of the notifications includes updating a visual color of a notification, or displaying a flash, banner, overlay, and/or other visual effect for the respective notification. For example, urgent notifications (e.g., the fourth and second visually adjusted manifestations of the notifications (410-2 and 410-4)) may be assigned a red color, flash, appear as a banner, overlay (i.e., over other display portions of the PCD 12), and/or include other effects. Similarly, the other notifications can be assigned different respective colors, flashes, banners, and/or visual effects. For example, an intermediate urgency notification may be yellow (e.g., the fifth visually adjusted notification 410-5) while routine and/or informational notifications are green (e.g., the third visually adjusted manifestations of the notification 410-3). Alternatively or additionally, in some implementations, routine and/or informational notifications are adjusted to appear without a color or without any specific color. In some implementations, the manifestations of the notifications are visually adjusted to accommodate for a user's disabilities and/or impairments. For example, if a user 210 is color blind, partially blind, or has other conditions, the PCD 12 can visually adjust a notification such that the user 210 can respond to the notifications and understand its level of urgency. Alternatively or additionally, in some implementations, the PCD 12 avoids one or more visual adjustments to a notification based on the user's disabilities and/or impairments. The one or more visual adjustments to the manifestations are configure to comply with the standards set for in IEC 60601.

In some implementations, the visually adjusted manifestations of the notifications 410 include information corresponding to the notification, a PCD 12, patient, a room, and/or other relevant information to the user 210. For example, the fourth visually adjusted manifestations of the notification includes the notification itself (illustrated by "Visual Notification 4"), the PCD 12 generating the alarm (e.g., "PCD 2"), and/or the particular module (e.g., functional modules 16, 18, 20, and 22; FIG. 1) of the PCD generating the notification (e.g. "Channel C").

In some implementations, the determined notification priorities include identify priorities between urgent notifications, between intermediate notifications, and/or between routine notifications. In some implementations, notifications with the same level of urgency are displayed in the order they are received. For example, the fourth and second visually adjusted manifestations of the notifications 410-2 and 410-4 are both urgent; however, because the fourth notification 410-4 may have been received before the second notification 410-2 it appears on top (i.e., notices that have gone longer periods of time without being acknowledged will be prioritized). In some implementations, notifications of the urgency level are presented alongside each other (e.g., side by side). Alternatively, in some implementations, notifications with the same level of urgency are displayed in order based on proximity (e.g., a PCD 12 will display a locally generated notification before a notification generated by another PCD 12 if the notification have the same level of urgency). In some implementations, prioritization of a notification is based on the dime of day. For example, during the day locally generated notifications by a PCD 12 are displayed before notifications generated by another PCD 12 (e.g., remotely generated notifications). In another example, during the night, locally generated notifications by a PCD 12 are displayed after notifications generated by another PCD 12 (e.g., remotely generated notifications).

The notification overview 400 further shows one or more audible manifestations of the notifications 420 generated by the PCD 12. In particular, the PCD 12 generates a first, second, third, and nth audibly adjusted manifestations of notifications 420-1, 420-2, 420-3, and 410-n (where n is an integer greater than zero). In the notification overview 400, the second audibly adjusted manifestations of the notification 420-2 is determined to be more urgent than the first, third, and nth audibly adjusted manifestations of the notifications 420-1, 420-3, and 420-n. The third audibly adjusted manifestations of the notification 420-3 is determined to be more urgent than the first and nth audibly adjusted manifestations of the notifications 420-1 and 420-n. The first and nth audibly adjusted manifestations of the notifications 420-1 and 420-n are determined be of equal urgency (or the first audibly adjusted notification 420-1 is slightly more urgent than the nth audibly adjusted notification 420-n). In some implementations, the urgency of a notification is communicated to the user 210 via adjustments to the audible notifications 420.

In some implementations, adjustments to the audible manifestations of the notifications include changes to the volume, tone, pitch, patterns, and/or rate of a notification. For example, the second audibly adjusted manifestations of the notification 420-2 can be set at a higher volume than the other audibly adjusted manifestations of the notifications 420 and/or be adjusted to play as a continuous sound without breaks. As another example, the third audibly adjusted manifestations of the notification 420-3 can be set to have a unique recognizable patter and/or include a distinct pitch and/or tone. In some implementations, the adjustment to audible manifestations of the notifications are specific to a PCD 12. More specifically, each PCD 12 can have its own audible notification (e.g., pattern, pitch, tone, rate, etc.), and adjustments to the audible manifestations of the notification are made such that the PCD's unique audible is still recognizable. For example, third audibly adjusted manifestations of the notification 420-3 can have its own unique pattern (illustrated by the pattern of two, one, and two music chords) and the first audibly adjusted manifestations of the notification 420-1 can have its own unique pattern (illustrated by the pattern of one, one, and one music chords), when the PCD 12 adjusts the third audibly adjusted manifestations of the notification 420-3 to make it more prominent than the first audibly adjusted manifestations of the notification 420-1, a volume or pitch adjustment can be made to the third audibly adjusted manifestations of the notification 420-3.

In some implementations, the notifications are audibly adjusted manifestations to accommodate for a user's disabilities and/or impairments. For example, if a user 210 is deaf in one ear, cannot hear certain frequencies, or has other conditions, the PCD 12 can audibly adjust manifestations of a notification such that the user 210 can respond to the notifications and understand its level of urgency. Alternatively or additionally, in some implementations, the PCD 12 avoids one or more audible adjustments to manifestations of a notification based on the user's disabilities and/or impairments. The one or more audible adjustments are configure to comply with the standards set for in IEC 60601.

In some implementations, a user 210 selects the visual and/or audio manifestations of the notification associated with a particular PCD 12 and/or urgency level. In this way, the user 210 can easily determine the PCDs 12 presenting audio manifestations of the notifications and/or the urgency of level of a notification. Alternatively or additionally, in some implementations, the audible manifestations of the notifications 420 can be adjusted to include a brief verbal cue. For example, the second audibly adjusted manifestations of the notification 420-2 can include a voice that reads out a room number. In some implementations, one or more visual and/or audible adjustments to manifestations of a notification are suggested to a user. The suggested visual and/or audible adjustments to manifestations of a notification are based, in part, on user 210 response time.

In some implementations, a single event can include visually adjusted manifestations of the notification 410 and audibly adjusted manifestations of the notification 420. Alternatively, in some implementations, a notification event can include either visually adjusted manifestations of the notification 410 or audibly adjusted manifestations of the notification 420 (but not both). In some implementations, a notification event includes only visual manifestations of the notification and no audible manifestations of the notification, and vice versa.

Figure 5A:
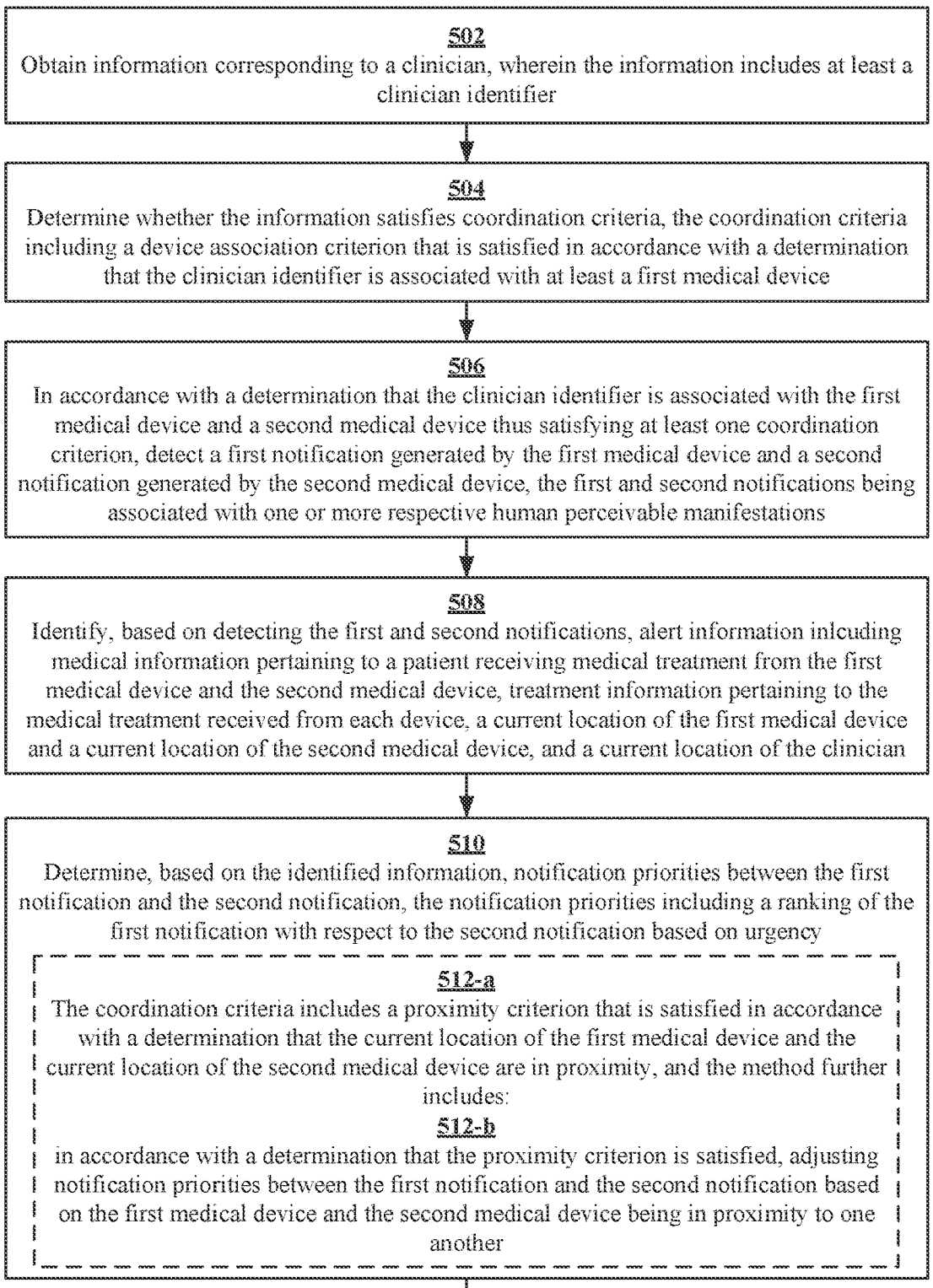
Figure 6:
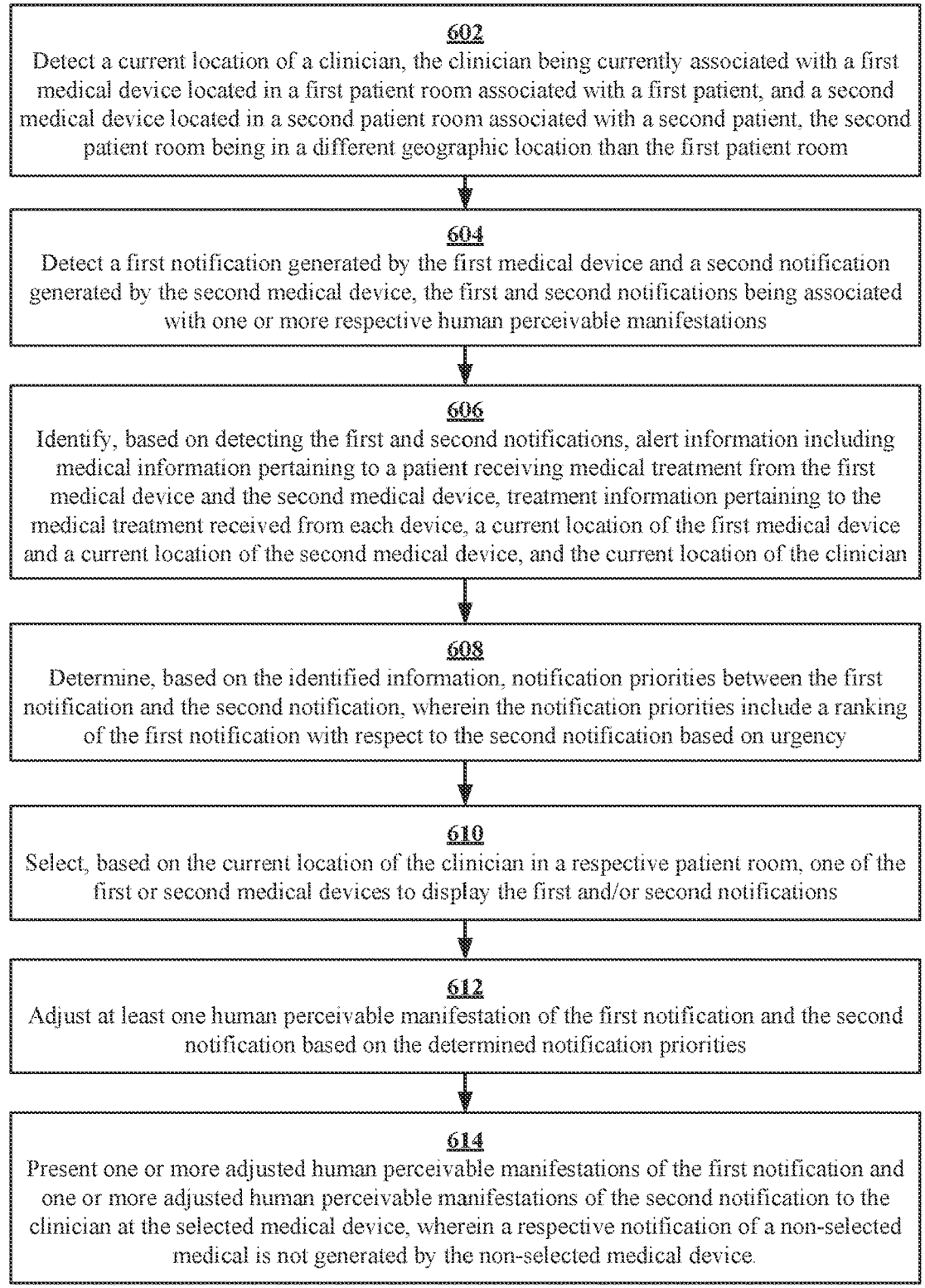
FIG. 6 is another flowchart illustrating a method for managing alarms between patient care devices, according to various aspects of the subject technology.

FIGS. 5A-6 are flowcharts illustrating methods for coordinating and managing notifications between a network of PCDs according to some implementations. The methods may be performed at one or more device terminals, patient care units 12, and/or server 30. More specifically, the operations of the methods are performed by a computer having a processor executing commands stored in a memory of the computer (e.g., CPU 50, and database 56). In some implementations, information is transmitted between one or more devices in a system (e.g., server 30 and PCDs 12), such as patient information, user information, notification information, and/or user input information. The operations of the methods consistent with the present disclosure may include at least some, but not all, of the operations performed in a different sequence. Similarly, one or more operations illustrated in FIGS. 5A-6 may be optional. Furthermore, the operations of the methods consistent with the present disclosure may include at least two or more steps performed overlapping in time, or almost simultaneously.

The method 500 includes obtaining (502) information corresponding to a clinician, the information including at least a clinician identifier (e.g., a UID, RFID, etc.). More specifically, the method includes obtaining clinician data for a user 210 (FIG. 2) that can be used to identify and/or authenticate a user 210. In some implementations, the clinician data is in database 56 internal to the PCD 12, and/or the external database 37 (FIG. 1). The information corresponding to the clinician includes a user's 210 association with one or more medical devices (e.g., PCDs 12) and/or association with one or more patients 220 (FIG. 2). The information corresponding to the clinician includes other data specified above in reference to FIG. 1. The method 500 includes determining (504) whether the information satisfies coordination criteria. The coordination criteria include a device association criterion that is satisfied in accordance with a determination that the clinician identifier is associated with at least a first medical device.

The method 500 includes, in accordance with a determination that the clinician identifier is associated with the first medical device and a second medical device thus satisfying at least one coordination criterion, detecting (506) a first notification generated by the first medical device and a second notification generated by the second medical device. The first and second notifications are associated with one or more respective human perceivable manifestations. The method 500 further includes identifying (508), based on detecting the first and second notifications, alert information including medical information pertaining to a patient receiving medical treatment from the first medical device and the second medical device, treatment information pertaining to the medical treatment received from each device, a current location of the first medical device and a current location of the second medical device, and a current location of the clinician. A non-exhaustive list of medical information includes patient conditions, disorders, sicknesses, illnesses, diseases, and/or other ailments. A non-exhaustive list of treatment information includes infusion drugs or fluids administered to a patient, treatment duration, volume to be infused (VTBI), flow rate, and other treatment information. The current location of the clinician may include geo locations, patient room, building, treatment areas (e.g., ICU, operating room, etc.), or other locations.

The method 500 includes determining (510), based on the identified information, notification priorities between the first notification and the second notification. The notification priorities including a ranking of the first notification with respect to the second notification based on urgency. In some implementations, when the first medical device and/or the second medical device is an infusion pump, the notification priorities between the first notification and the second notification are based, in part, on a type drug, duration of infusion, and/or time remaining for infusion. In some implementations, the notification priorities between the first notification and the second notification are based, in part, on one or more alarm types.

In some implementations, the coordination criteria includes (512-a) a proximity criterion that is satisfied in accordance with a determination that the current location of the first medical device and the current location of the second medical device are in proximity, and the method 500 further includes, in accordance with a determination that the proximity criterion is satisfied, adjusting (512-b) notification priorities between the first notification and the second notification based on the first medical device and the second medical device being in proximity to one another. For example, the first and second medical devices can be adjacent to one another; in the same room; and/or on the same floor, and the notification priorities can be adjusted such that notifications for the first and medical device are grouped together (if they can be addressed in the same time window (e.g., within 5 min.)). In some implementations, the coordination criteria includes (514-a) a remote criterion that is satisfied in accordance with a determination that the current location of the first medical device and the current location of the second medical device are remote, and the method further includes, in accordance with a determination that the remote criterion is satisfied, adjusting (514-b) notification priorities between the first notification and the second notification based on the first medical device and the second medical device being remote to one another. For example, the first and second medical devices can be on different floors; in different wings of a building; and/or in different buildings, and the notification priorities can be adjusted such that notifications for the first and second medical device are prioritized efficiently (i.e., allowing the user 210 to address notifications based on urgency without causing the user to spend additional time going back and forth).

In some implementations, the coordination criteria includes (516-a) a patient association criterion that is satisfied in accordance with a determination that the first medical device and the second medical device are associated with the same patient, and the method further includes, in accordance with a determination that the patient association criterion is satisfied, adjusting (516-b) notification priorities between the first notification and the second notification based on the first medical device and the second medical device being associated with the same patient. For example, if the first and second medical devices are associated with the same patient(s), the notification priorities can be adjusted such that notifications for the first and medical device are grouped together (if they can be addressed in the same time window (e.g., within 5 min.)). Alternatively, in some implementations, the method includes, in accordance with a determination that the patient association criterion is not satisfied, adjusting (518) notification priorities between the first notification and the second notification based on the first medical device and the second medical device being associated with distinct patients. More specifically, the notification priorities can be adjusted such that notifications for the first and medical device are prioritized efficiently (i.e., allowing the user 210 to address notifications based on urgency without causing the user to waste time going back and forth).

The method 500 includes adjusting (520) at least one human perceivable manifestation of the first notification and the second notification based on the determined notification priorities. In some implementations, adjusting (522) the one or more human perceivable manifestations of the first notification and the second notification includes adjusting visual manifestations and/or audible manifestations of the first notification and the second notification. In some implementations, adjusting audible manifestations of the notifications of the first notification and the second notification includes changing the volume, pitch, rate, and/or tone of the first notification and the second notification. Alternatively or additionally, in some implementations, adjusting visual manifestations of the notifications of the first notification and the second notification includes updating a visual color of the first notification and the second notification, or displaying a flash and/or banner for the first notification and the second notification. In some implementations, adjusting (524) the one or more human perceivable manifestations of the first notification and the second notification based on the determined notification priorities includes adjusting one or more respective human perceivable manifestations notifications to emphasize higher ranked notifications over lower ranked notifications.

The method 500 further includes presenting (526) one or more adjusted human perceivable manifestations of the first notification and one or more adjusted human perceivable manifestations of the second notification to the user via one of the first medical device or the second medical device.

In some implementations, the first medical device and the second medical device are located (528-a) in a first patient room associated with a first patient, the method 500 further includes detecting (528-b) that the current location of the clinician is in a second patient room associated with a second patient, the second patient room being in a different geographic location than the first patient room. For example, the clinician may be in a different patient room on a different floor or on the same floor of the same hospital. In another example, the clinician may be in a patient room of a different hospital. As described herein, the clinician may be proximate or remote to a patient and/or medical device. The method 500 further includes selecting (528-c), based on the determining of the notification priorities, one of the first or second notifications for display at a third medical device located in the second patient room while the clinician is in the second patient room. The method includes presenting (528-d) one or more respective adjusted human perceivable manifestations of the selected notification at the third medical device while the clinician is in the second patient room, the first notification and the second notification are not presented at the first medical device and the second medical device while the selected notification is presented at the third medical device. In some implementations, the one or more human perceivable manifestations of a third notification are received (530-*a*) at the third medical device such that the one or more human perceivable manifestations of the third notification are set for presentation by the third medical device during a period of time in which the one or more human perceivable manifestations of the first notification or the one or more human perceivable manifestations of the second notification are generated by the first medical device or the second medical device, respectively. The method 500 further includes overriding (530-*b*) the presentation of the one or more human perceivable manifestations of the third notification with the one or more respective adjusted human perceivable manifestations of the selected notification such that the selected notification is presented at the third medication device while the clinician is in the second patient room.

In some implementations, the method 500 includes determining (532-*a*) respective user response times to the adjusted one or more human perceivable manifestations of the first notification and the adjusted one or more human perceivable manifestations of the second notification. The method 500 further includes identifying (532-*b*) a respective adjustment to the one or more human perceivable manifestations of the first notification and the one or more human perceivable manifestations of the second notification with the lowest user response time. The method 500 includes adjusting (532-*c*) subsequent human perceivable manifestations of the first notification and subsequent human perceivable manifestations of the second notification based on the determined notification priorities and adjustments to the one or more human perceivable manifestations with the lowest user response time. In this way, urgent notifications are adjusted to have the lowest user response time.

In some implementations, the method 500 includes detecting (534-*a*) a third notification generated by a third medical device, and, in accordance with a determination that the clinician identifier is associated with the third medical device, determining (534-*b*) the notification priorities between the first notification, the second notification, and the third notification. The method 500 further includes adjusting (534-*c*) one or more respective human perceivable manifestations of the first notification, the second notification, and the third notification based on the determined notification priorities, and presenting (534-*d*) the one or more adjusted human perceivable manifestations of the first notification, the one or more adjusted human perceivable manifestations of the second notification, and one or more adjusted human perceivable manifestations of the third notification to the user. In some implementations, the method 500 includes detecting (536-*a*) a fourth notification generated by the first or second medical device. The method includes 500 determining (536-*b*) the notification priorities between the first notification, the second notification, and the fourth notification; adjusting (536-*c*) the one or more human perceivable manifestations of the first notification, the one or more human perceivable manifestations of the second notification, and one or more human perceivable manifestations of the fourth notification based on the determined notification priorities. The method 500 further includes presenting (536-*d*) the one or more adjusted human perceivable manifestations of the first notification, the one or more adjusted human perceivable manifestations of the second notification, and one or more adjusted human perceivable manifestations of the fourth notification to the user.

In some implementations, another method 600 includes detecting (602) a current location of a clinician. The clinician may be currently associated with a first medical device located in a first patient room associated with a first patient, and a second medical device located in a second patient room associated with a second patient, the second patient room being in a different geographic location than the first patient room. For example, the first and second patient rooms may be in different buildings, different floors, different rooms on the same floor, and other variations. The method 600 includes detecting (604) a first notification generated by the first medical device and a second notification generated by the second medical device. The first and second notifications are associated with one or more respective human perceivable manifestations.

The method 600 includes identifying (606), based on detecting the first and second notifications, alert information including medical information pertaining to a patient receiving medical treatment from the first medical device and the second medical device, treatment information pertaining to the medical treatment received from each device, a current location of the first medical device and a current location of the second medical device, and the current location of the clinician. Examples of the alert information are provided above in reference to FIGS. 1 and 4-5D.

The method 600 includes determining (608), based on the identified information, notification priorities between the first notification and the second notification. The notification priorities include a ranking of the first notification with respect to the second notification based on urgency. The method 600 includes selecting (610), based on the current location of the clinician in a respective patient room, one of the first or second medical devices to display the first and/or second notifications. In this way, the method is able to select the medical device that is proximate to the clinician.

The method 600 includes adjusting (612) at least one human perceivable manifestation of the first notification and the second notification based on the determined notification priorities, and presenting (614) one or more adjusted human perceivable manifestations of the first notification and one or more adjusted human perceivable manifestations of the second notification to the clinician at the selected medical device. A respective notification of a non-selected medical is not generated by the non-selected medical device. More specifically, the method includes identifying the patient room that the clinician is in and providing the first and/or second notifications (based on the notification priorities) to the clinician via the medical device that the clinician is proximate to. For example, if the clinician is in the second patient room, notifications generated by the first medical device and the second medical device will both be provided to the clinician via the second medical device in the second patient room.

Figure 7:
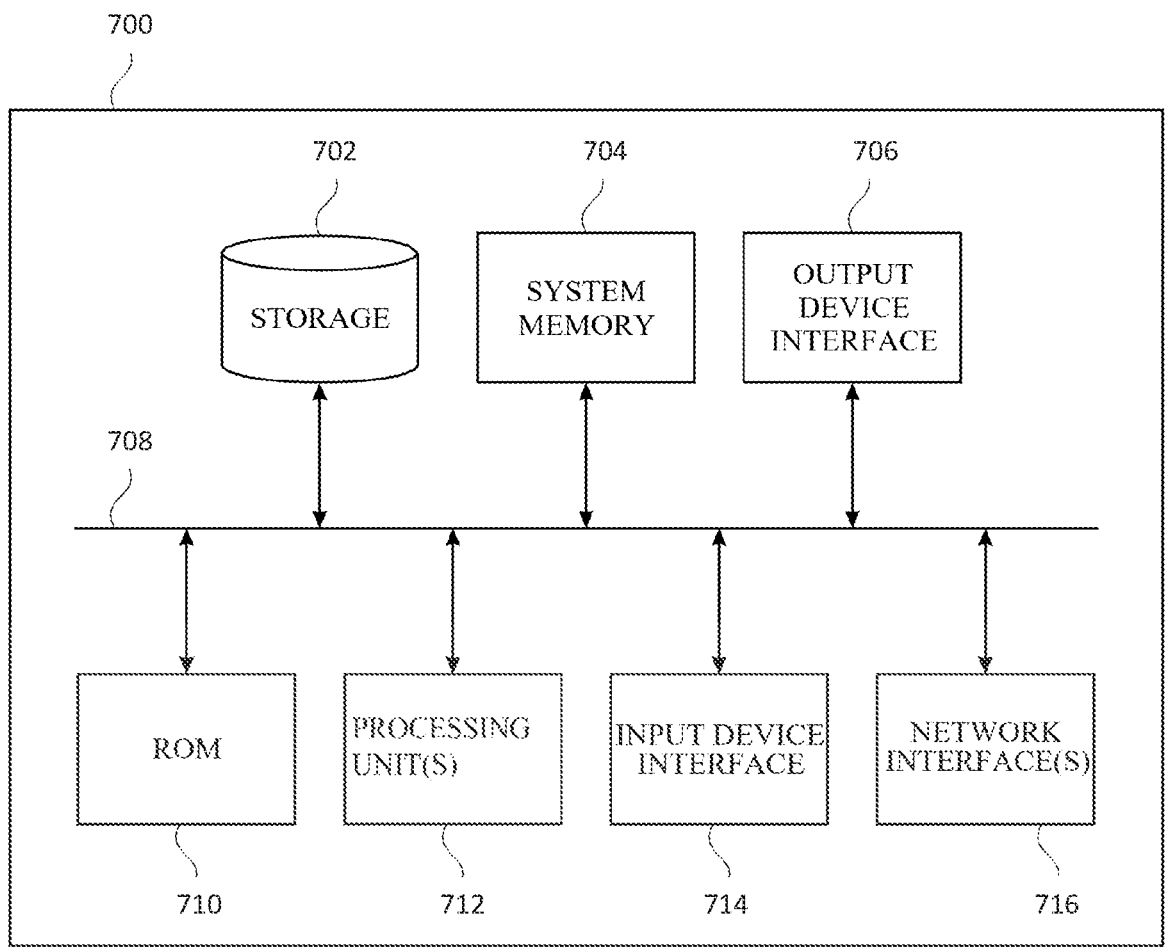
FIG. 7 is a conceptual diagram illustrating an example electronic system for implementing an alarm management system, according to various aspects of the subject technology.

FIG. 7 is a conceptual diagram illustrating an example electronic system 700 for implementing an alarm management system, according to various aspects of the subject technology. Electronic system 700 may be a computing device for execution of software associated with one or more portions or steps of processes 500 and 600, or components and processes provided by FIGS. 1-6. Electronic system 700 may be representative, in combination with the disclosure regarding FIGS. 1-5, of the alarm management system described above. In this regard, electronic system 700 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 700 may include various types of computer readable media and interfaces for various other types of computer readable media. In the depicted example, electronic system 700 includes a bus 708, processing unit(s) 712, a system memory 704, a read-only memory (ROM) 710, a permanent storage device 702, an input device interface 714, an output device interface 706, and one or more network interfaces 716. In some implementations, electronic system 700 may include or be integrated with other computing devices or circuitry for operation of the various components and processes previously described.

Bus 708 collectively represents all system, peripheral, and chipset buses that communicatively connect the numerous internal devices of electronic system 700. For instance, bus 708 communicatively connects processing unit(s) 712 with ROM 710, system memory 704, and permanent storage device 702.

From these various memory units, processing unit(s) 712 retrieves instructions to execute and data to process in order to execute the processes of the subject disclosure. The processing unit(s) can be a single processor or a multi-core processor in different implementations.

ROM 710 stores static data and instructions that are needed by processing unit(s) 712 and other modules of the electronic system. Permanent storage device 702, on the other hand, is a read-and-write memory device. This device is a non-volatile memory unit that stores instructions and data even when electronic system 700 is off. Some implementations of the subject disclosure use a mass-storage device (such as a magnetic or optical disk and its corresponding disk drive) as permanent storage device 702.

Some implementations use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such a random access memory. System memory 704 stores some of the instructions and data that the processor needs at runtime. In some implementations, the processes of the subject disclosure are stored in system memory 704, permanent storage device 702, and/or ROM 710. From these various memory units, processing unit(s) 712 retrieves instructions to execute and data to process in order to execute the processes of some implementations.

Bus 708 also connects to input and output device interfaces 714 and 706. Input device interface 714 enables the user to communicate information and select commands to the electronic system. Input devices used with input device interface 714 include, e.g., alphanumeric keyboards and pointing devices (also called "cursor control devices"). Output device interfaces 706 enables, e.g., the display of images generated by the electronic system 700. Output devices used with output device interface 706 include, e.g., printers and display devices, such as cathode ray tubes (CRT) or liquid crystal displays (LCD). Some implementations include devices such as a touchscreen that functions as both input and output devices.

Also, bus 708 also couples electronic system 700 to a network (not shown) through network interfaces 716. Network interfaces 716 may include, e.g., a wireless access point (e.g., Bluetooth or WiFi) or radio circuitry for connecting to a wireless access point. Network interfaces 716 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 700 can be used in conjunction with the subject disclosure.

Figure 8:
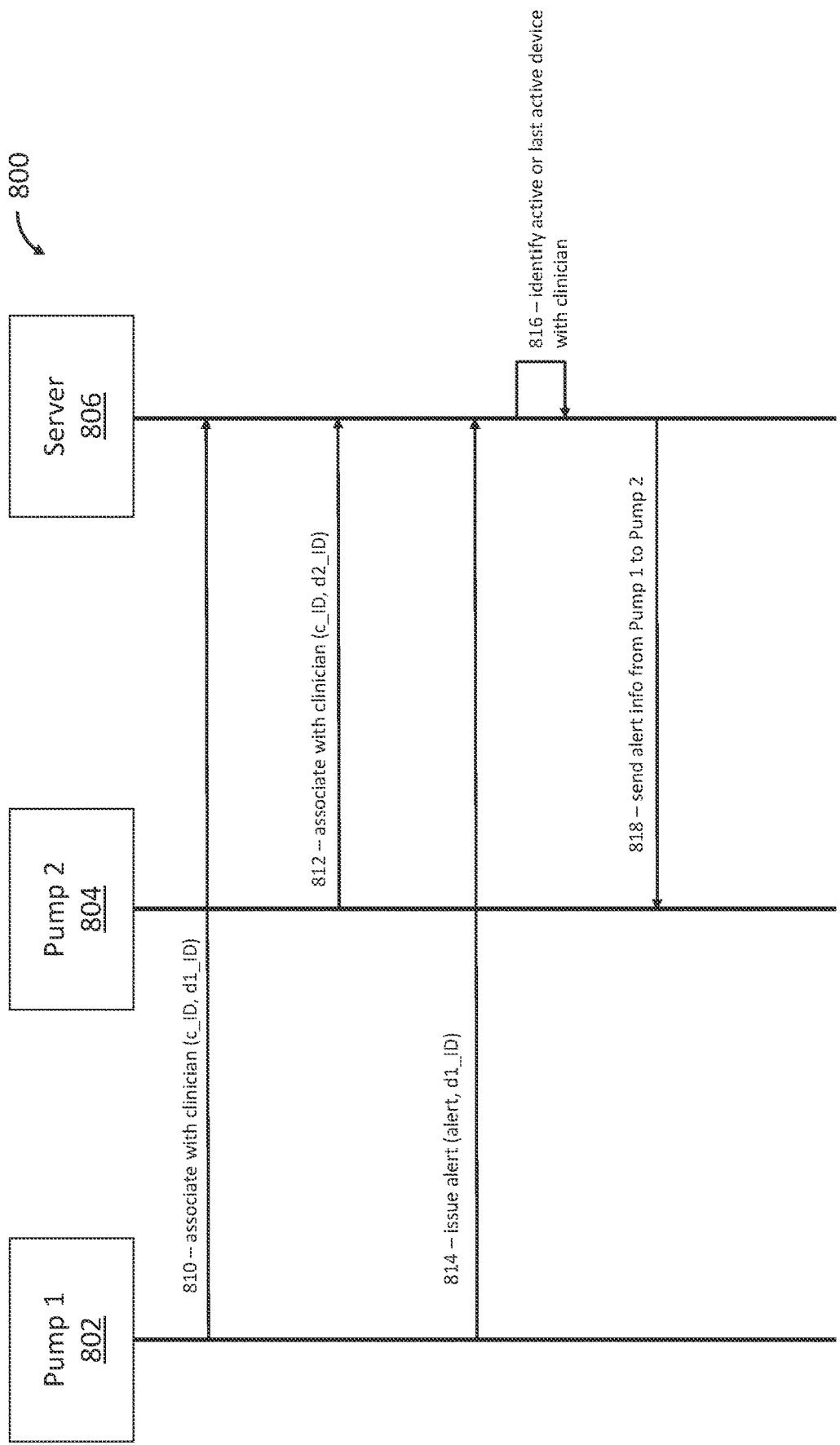
FIG. 8 is a first messaging diagram showing an example exchange of messages for coordinating alarms based on a clinician identifier, in accordance with some implementations.

FIG. 8 is a first messaging diagram showing an example exchange of messages for coordinating alarms based on a clinician identifier, in accordance with some implementations. The environment 800 in FIG. 8 includes one or more devices, such as a first pump 802 (e.g., a first PCD 12-1; FIG. 2); a second pump 804 (e.g., a second PCD 12-2; FIG. 2); and a server 806 (e.g., a server 30; FIG. 2). In some embodiments, the environment 800 is an example of part of the system 200 described above in reference to FIG. 2. In some implementations, the first pump 802 and the second pump 804 are physically separated devices that may, in some instances, provide fluids to different patients who are, in some instances, in different physical locations (e.g., different patient rooms). The one or more devices in FIG. 8 are shown exchanging messages directly however, in some implementations, the messages may be mediated or transmitted through one or more intermediary device such as a gateway, proxy server, security scanning device, access point, or other electronic communication device (e.g., via a network 10; FIG. 2). Although the environment 800 shows interactions between pumps, the coordination of alarms may be between additional or alternative medical devices such as an infusion pump, dispensing cabinet, or other device within the facility. The coordination may also be performed between medical devices of differing types. For example, a pump and a dispensing cabinet may coordinate presentation of alerts, alarms, or other notifications.

In the environment 800 of FIG. 8, the server 806 acts as a central clearing house for notification coordination. In some implementations, the server 806 tracks a clinician through the environment 800. If a device the clinician has previously associated with issues an alert, the server 806 may identify another device that the clinician is currently logged into (or the last device the clinician was actively using and/or logged into) and presents the alert via that other device.

In some implementations, the first pump 802 transmits a first message 810 to the server 806 to associate an identifier for the clinician ("c_ID") with an identifier for the first pump 802 ("d1_ID"). The clinician identifier may be provided when a user logs into the first pump 802. In some implementations, the identifier for the first pump 802 may include a unique identifier for the first pump 802, a network address for the first pump 802, or other information to distinguish and associated messages to or from the first pump 802 from messages associated with another device within the environment 800.

In some implementations, the server 806 stores the association record (between the first pump 802 and the clinician) in a data store. The association may be stored for a configurable period of time (e.g., 30 minutes). The association may be stored for a dynamic period of time such as based on a work schedule of the identified clinician. For example, if the clinician is scheduled to stop work or take a break at a certain time, the association may be stored until that certain time arrives. In some implementations, if the server 806 detects that the clinician logs out of a device (e.g., the first pump 802), the period of time the association is maintained may be stored for a threshold period of time. The threshold period of time may be configured such that if an alert is forwarded to the most recently active device, it is done within a period of time that is likely to correspond with the clinician being proximate to the logged out device (e.g., 1 minute, 5 minutes, 30 minutes, etc.). In some implementations, the clinician actively or passively logs out of the first pump 802. For example, the clinician may leave a first patient room where the first pump 802 is located and travel to a second location (e.g., a second patient room) where the second pump 804 is located. The server 806 may keep the association record between the first pump 802 and the clinician but indicate the clinician is not actively using the first pump 802.

In some implementations, the second pump 804 transmit a second message 812 to the server 806 to associate an identifier for the clinician ("c_ID") with an identifier for the second pump 804 ("d2_ID"). As described above with reference to the first message 810, the association (between the second pump 804 and the clinician) may be stored by the server 806. In some implementations, when the clinician is associated with the second pump 804, the server 806 updates the association record for the clinician and first pump 802 to indicate the clinician is not actively using the first pump 802. Similarly, the association between the second pump 804 and the clinician may be marked as active.

While the clinician is active at the second pump 804 or before the clinician switches activity to another pump, the first pump 802 may transmit an alert message 814 to the server 806. The alert message 814 may include information about the alert ("alert") along with information to identify the first pump 802 as the source of the alert ("d1_ID"). In some implementations, the server 806, via a third messaging 816, may identify the current device for the clinician who is associated with the first pump 802. In some implementations, identifying the current device for a clinician who is associated with a respective pump (e.g., the first pump 802) includes determining one or more clinician identifiers associated with the device identifier for the respective pump. With the clinicians identified, the server 806 may then determine which devices an identified clinician is actively using or, if not actively using a device, the device that was most recently used by the clinician. In the example shown, the clinician is active or was recently active on the second pump 804.

Based at least on the second identifier for the second pump 804, the server 806 may transmit a fourth message 818 to the second pump 804. The fourth message 818 may include all or a portion of the alert received via the alert message 814. In some implementations, the fourth message 818 may include information identifying or associated with the first pump 802 to provide context to the alert that may be presented on the second pump 804. In the case where multiple clinicians were previously associated with the first pump 802, the server 806 may transmit alternate or additional messages to respective active devices associated with the multiple clinicians. After receiving the alert, the second pump 804 may enable (or make active) one or more user interface element (e.g., display, audio device, etc.) to present information about the alert.

Figure 9:
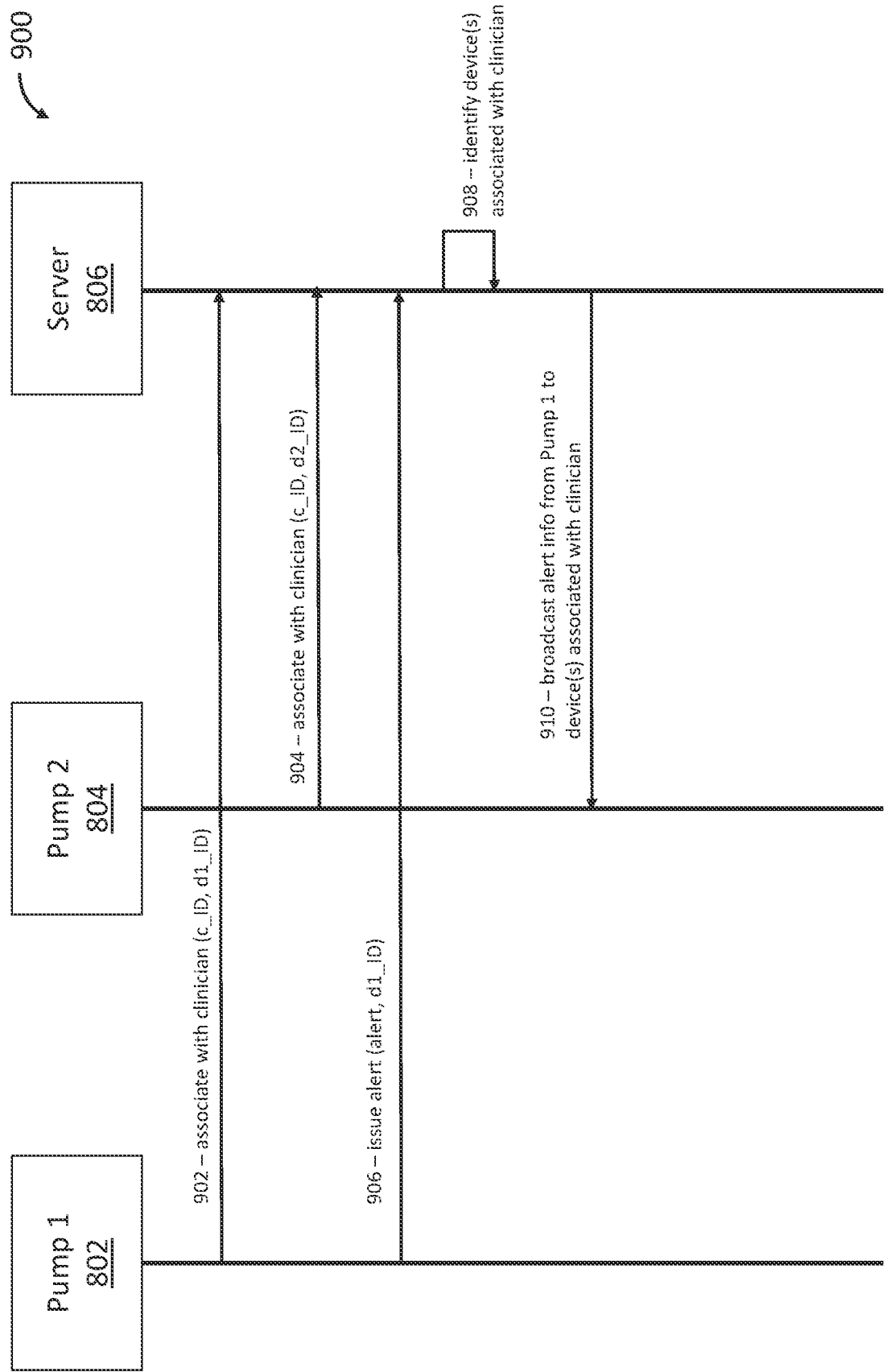
FIG. 9 is second a messaging diagram showing an example exchange of messages for coordinating alarms based on a clinician identifier, in accordance with some implementations.

FIG. 9 is a second messaging diagram showing an example exchange of messages for coordinating alarms based on a clinician identifier, in accordance with some implementations. The environment 900 in FIG. 9 includes a first pump 802, a second pump 804, and a server 806. In some embodiments, the environment 900 is an example of part of the system 200 described above in reference to FIG. 2. In some implementations, environment 900 is configured to exchange one or more messages as described above in reference to FIG. 8. Although the environment 900 shows interactions between pumps, the coordination of alarms may be between additional or alternative medical devices such as an infusion pump, dispensing cabinet, or other device within the facility. The coordination may also be performed between medical devices of differing types. For example, a pump and a dispensing cabinet may coordinate presentation of alerts, alarms, or other notifications. Similar to FIG. 8, the server 806 acts as a central clearing house for notification coordination, tracks a clinician through the environment 900, identifies a device actively used by a clinician to provide an alert generated by another device, and/or identifies a set of devices that clinician is associated with and present the alert to the set of devices.

In some implementations, the first pump 802 transmits a first message 902 to the server 806 to associate an identifier for the clinician ("c_ID") with an identifier for the first pump 802 ("d1_ID"). The clinician identifier may be provided when a user logs into the first pump 802. In some implementations, the identifier for the first pump 802 includes a unique identifier for the first pump 802, a network address for the first pump 802, or other information to distinguish and associated messages to or from the first pump 802 from messages associated with another device within the environment 900. In some implementations, the server 806 stores the association record (between the first pump 802 and the clinician) in a data store. The association may be stored for a configurable period of time (e.g., 30 minutes). The association may be stored for a dynamic period of time such as based on a work schedule of the identified clinician. For example, if the clinician is scheduled to stop work or take a break at a certain time, the association may be stored until that certain time arrives.

In some implementations, the second pump 804 transmits a second message 904 to the server 806 to associate an identifier for the clinician ("c_ID") with an identifier for the second pump 804 ("d2_ID"). As described above with reference to the first message 902, the association may be stored by the server 806. When the clinician is associated with the second pump 804, the server 806 may update the association record for the clinician and first pump 802 to indicate that the clinician is not actively using the first pump 802. Similarly, the association between the second pump 804 and the clinician may be marked as active.

In some implementations, the first pump 802 transmits an alert message 906 to the server 806. The alert message 906 may include information about the alert ("alert") along with information to identify the first pump 802 as the source of the alert ("d1_ID"). In some implementations, the server 806, via a third message 908, may identify the clinician who is associated with the first pump 802. Identifying the clinician may include determining one or more clinician identifiers associated with the device identifier for the first pump 802. With the clinicians identified, the server 806 may then determine which devices are associated with an identified clinician. In the example shown, the clinician is associated with the second pump 804.

Based at least on the second identifier for the second pump 804, the server 806 may transmit a fourth message 910 to the second pump 804. The fourth message 910 may include all or a portion of the alert received via the alert message 906. In some implementations, the fourth message 910 may include information identifying or associated with the first pump 802 to provide context to the alert that may be presented on the second pump 804. In the case where multiple clinicians were previously associated with the first pump 802, the server 806 may transmit alternate or additional messages to respective devices associated with the multiple clinicians. The server 806 may omit transmitting the fourth message 910 to the source of the alert the first pump 802). In some implementations, transmitting the fourth message 910 includes broadcasting a message including an identifier that receiving pumps can detect to filter alerts targeted at the pump. In some implementations, transmitting the fourth message 910 includes point to point or limited group messaging to only the associated devices. After receiving the alert, the second pump 804 may enable (or make active) one or more user interface element (e.g., display, audio device, etc.) to present information about the alert.

Figure 10:
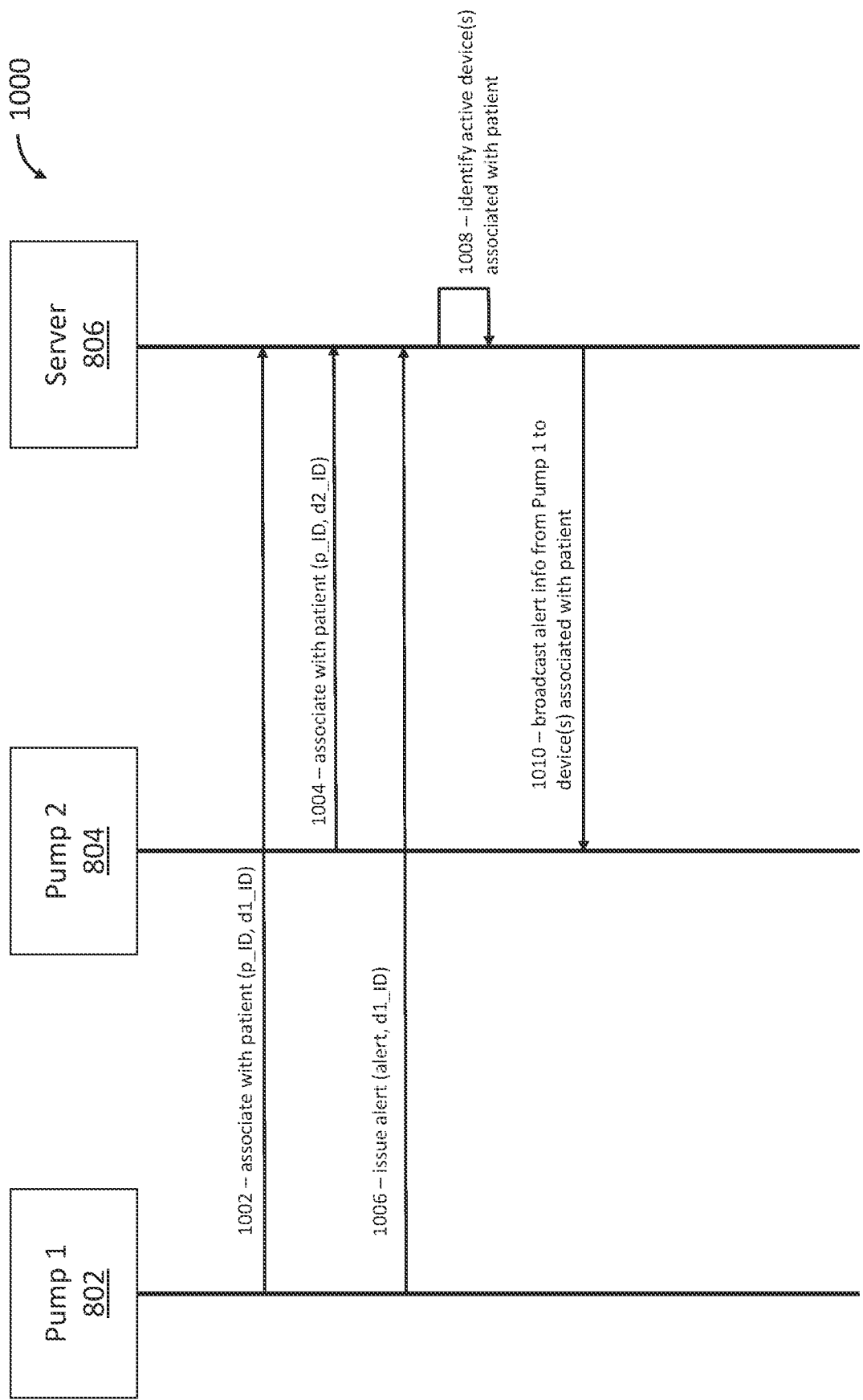
FIG. 10 is a messaging diagram showing an example exchange of messages for coordinating alarms based on a patient identifier, in accordance with some implementations.

FIG. 10 is a messaging diagram showing an example exchange of messages for coordinating alarms based on a patient identifier, in accordance with some implementations. In some implementations, the environment 1000 in FIG. 10 includes a first pump 802, a second pump 804, and a server 806 similar to FIG. 8. In some embodiments, the environment 1000 is an example of part of the system 200 described above in reference to FIG. 2. The first pump 802 and the second pump 804 are physically separated devices that may, in some instances, be providing fluids to the same patient. The devices in FIG. 10 are shown exchanging messages directly however, in some implementations, the messages may be mediated or transmitted through one or more intermediary device such as a gateway, proxy server, security scanning device, access point, or other electronic communication device (e.g., via a network 10; FIG. 2). Although the environment 1000 shows interactions between pumps, the coordination of alarms may be between additional or alternative medical devices such as an infusion pump, dispensing cabinet, or other device within the facility. The coordination may also be performed between medical devices of differing types. For example, a pump and a dispensing cabinet may coordinate presentation of alerts, alarms, or other notifications.

In the environment 1000 of FIG. 10, the server 806 acts as a central clearing house for notification coordination. The server 806 tracks a clinician through the environment 900. Where the server 806 in FIGS. 8 and 9 coordinated alerts based on clinician identifier, in the example messaging in FIG. 10, the server 806 coordinates alerts based on association with a common patient identifier. It will be understood that the features of FIG. 10 may be used in combination with the features of FIG. 8 or 9 to coordinate alarms based on clinician identifier along with patient identifier.

In some implementations, the first pump 802 transmits a first message 1002 to the server 806 to associate an identifier for the patient ("p_ID") with an identifier for the first pump 802 ("d1_ID"). In some implementations, the patient identifier is provided when a user scans a barcode or wireless tag for the patient. The scanned information may be directly or indirectly provided to the first pump 802. In some implementations, the identifier may be entered into the first pump 802 via a graphical user interface. The identifier for the first pump 802 may include a unique identifier for the first pump 802, a network address for the first pump 803, or other information to distinguish and associated messages to or from the first pump 802 from messages associated with another device within the environment 1000. In some implementations, the server 806 stores the association record in a data store. The association may be stored for a configurable period of time 30 minutes). The association may be stored for a dynamic period of time such as based on a therapy schedule for the identified patient. For example, if the patient is scheduled to change care areas at a certain time (e.g., go to therapy, discharge, change rooms, etc.), the association may be stored until that certain time arrives. In some implementations, the association is removed once a new patient is associated with the device. In such implementations, the relationship between patients and devices is one to many (e.g., one patient may be associated to one or devices at one time). In such implementations, one device cannot be associated with more than one patient at a time. In some implementations, the association may be removed when the device is no longer actively delivering a medication or other therapy to the patient. The device may provide one or more messages indicating the end of delivery. The server 806 may detect this message and remove the association between the device and the patient.

In some implementations, the second pump 804 transmits a second message 1004 to the server 806 to associate an identifier for the patient ("p_ID") with an identifier for the second pump 804 ("d2_ID"). As described above with reference to the first message 1002, the association may be stored by the server 806.

In some implementations, the first pump 802 transmits an alert message 1006 to the server 806. The alert message 1006 may include information about the alert ("alert") along with information to identify the first pump 802 as the source of the alert ("d1_ID"). The server 806, via a third message 1008, may identify the patient who is associated with the first pump 802. In some implementations, identifying the patient includes determining one or more patient identifiers associated with the device identifier for the first pump 802. With the patient identified, the server 806 may then determine which devices are actively associated with an identified patient. In the example shown, the patient is actively associated with the second pump 804.

Based at least on the second identifier for the second pump 804, the server 806 may transmit a fourth message 1010 to the second pump 804. In some implementations, the fourth message 1010 includes all or a portion of the alert received via the alert message 1006. In some implementations, the fourth message 1010 includes information identifying or associated with the first pump 802 to provide context to the alert that may be presented on the second pump 804. In the case where the patient is associated with multiple devices, which are actively associated with the patient, the server 806 may transmit alternate or additional messages to respective devices associated with the patient. A patient may have an active association with a device when the device is in the process of delivering a medication or other therapy to the patient. The server 806 may omit transmitting the fourth message 1010 to the source of the alert (i.e., the first pump 802). Transmitting may include broadcasting a message including an identifier that receiving pumps can detect to filter alerts targeted at the pump. Transmitting may include point to point or limited group messaging to only the associated devices. After receiving the alert, the second pump 804 may enable (or make active) one or more user interface element (e.g., display, audio device, etc.) to present information about the alert.

Figure 11:
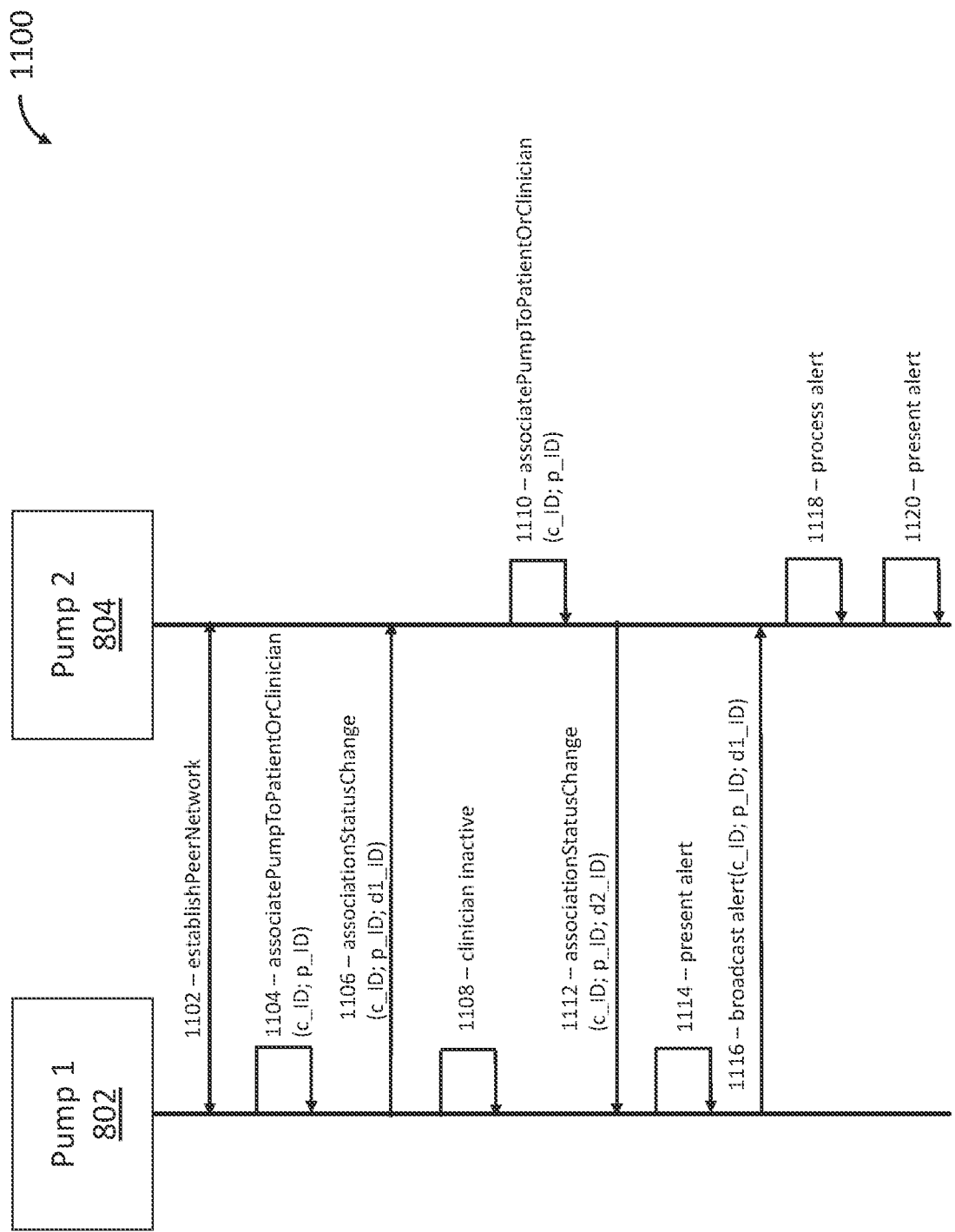
FIG. 11 is a messaging diagram showing an example exchange of messages for coordinating alarms using a peer-to-peer network, in accordance with some implementations.

FIG. 11 is a messaging diagram showing an example exchange of messages for coordinating alarms using a peer-to-peer network, in accordance with some implementations. The environment 1100 in FIG. 11 includes the first pump 802 and the second pump 804. In some embodiments, the environment 1100 is an example of part of the system 200 described above in reference to FIG. 2. The first pump 802 and the second pump 804 are physically separated devices that may, in some instances, be providing fluids to different patients who are, in some instances, in different physical locations (e.g., different patient rooms). The devices in FIG. 11 are shown exchanging messages directly however, in some implementations, the messages may be mediated or transmitted through one or more intermediary device such as a gateway, proxy server, security scanning device, access point, or other electronic communication device. Although the environment 1100 shows interactions between pumps, the coordination of alarms may be between additional or alternative medical devices such as an infusion pump, dispensing cabinet, or other device within the facility. The coordination may also be performed between medical devices of differing types. For example, a pump and a dispensing cabinet may coordinate presentation of alerts, alarms, or other notifications.

Unlike the environments 800, 900, or 1000 of FIGS. 8, 9, and 10, the environment 1100 does not require a server. Instead, the devices self-organize a peer-to-peer fashion to coordinate alerts, alarms, or other notifications. The devices each have respective user interfaces to present alerts, alarms, or other notifications. The environment 1100 shows how a device may "lend" its interface to present an alert generated by another device with a common interest (e.g., common patient or clinician operator).

In some implementations, the first pump 802 and the second pump 804, via a first message 1102, establish a peer network. Establishing a peer network may include exchanging tokens, keys, and identifiers to confirm the authority and authenticity of devices joining the network. The peer network may be established using a standardized protocol such as BLUETOOTH 2.1, secure simple pairing (SSP), extensible messaging protocols (e.g, IETF XMPP), session initiation protocols (e.g., IEFT SIP or ITU H.323), or the like. The peer network may be established using proprietary messages to connect devices.

In some implementations, via a second message 1104, the first pump 802 may associate with a patient or clinician. The second message 1104 may include associating an identifier for the patient ("p_ID") and/or the clinician ("c_ID") interacting with the first pump 802. The patient identifier or clinician identifier may be provide as described with reference to FIG. 8, 9, or 10.

In some implementations, the first pump 802 transmits an association status change message 1106 to its peer devices. As shown in FIG. 11, the status change message 1106 is transmitted to the second pump 804. In some implementations, the status change message 1106 is transmitted directly to the peer devices. In some implementations, the status change message 1106 is broadcasted. In broadcast mode, receiving devices may process messages that do not include device identifiers ("d1_ID") in their active peer network. In some implementations, the status change message 1106 includes an identifier for the peer group.

In some implementations, via a third message 1108, the first pump 802 determines that the clinician is inactive with the first pump 802. The determination may be based on a log out or locking of the first pump 802. The determination may be based on a period of inactivity at the first pump 802. The determination may be based on receiving an indication that the clinician logged into another device within the environment 1100.

In some implementations, via a fourth message 1110, the second pump 804 is associated with the patient or the clinician. The fourth message 1110 may include associating the identifier for the patient ("p_ID") and/or the clinician ("c_ID") interacting the second pump 802. The patient identifier or clinician identifier may be provide as described with reference to FIG. 8, 9, or 10.

In some implementations, the second pump 804 transmits an association status change message 1112 to its peer devices. As shown in FIG. 11, the association status change message 1112 is transmitted to the first pump 802. In some implementations, the association status change message 1112 is transmitted directly to the peer devices. In some implementations, the association status change message 1112 is broadcasted. In broadcast mode, receiving devices may process messages that do not include device identifiers ("d2_ID") in their active peer network. In some implementations, the association status change message 1112 includes an identifier for the peer group.

At this stage, the environment 1100 is configured to allow the first pump 802 to present alerts it generates or that are generated by its peers (e.g., the second pump 804). Similarly, the second pump 804 can present alerts it generates or that are generated by its peers (e.g., the first pump 802). In the example shown in FIG. 11, via another alert message 1114, the first pump 804 presents an alert. The alert may identify a condition at the first pump 802 needing attention such as occlusion of an infusion line, air detected in the infusion line, infusion ending, infusion ended, power condition, or the like. Presenting the alert at the other alert message 1114 includes transmitting an audio or a visual indicator of the condition using one or more interface elements of the first pump 802.

Via a fifth message 1116, the first pump 802 broadcasts the alert to its peers. The fifth message 1116 includes one or more of the clinician identifier ("c_ID"), the patient identifier ("p_ID"), or the identifier of the first pump 802 ("d1_ID"). In some implementations, the fifth message 1116 is be transmitted until a threshold period of time elapses from presentation of the alert via the other alert messaging 1114 (e.g., thirty seconds, one minute, or five minutes).

The second pump 804, via a sixth message 1118, processes the alert to determine whether the alert should be presented using one or more interface elements of the second pump 804. The processing may include determining if the alert is from a device within the active peer group of the second pump 804. If the alert is not associated with the peer group, the second pump 804 may take no further action for the fifth message 1116. However, if the fifth message 1116 related to the peer group, via seventh message 1120, the second pump may present all or a portion of the alert. Presenting the alert at the seventh message 1120 may include transmitting an audio or a visual indicator of the condition using one or more interface elements of the second pump 804. This provides a second manifestation via a different device for the alert.

These features described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, audible feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Aspects described include artificial intelligence or other operations whereby the system processes inputs and generates outputs with apparent intelligence. For example, the systems and methods disclosed herein can determine adjustments to manifestations of notifications based on clinician inputs to reduce clinician response time in responding to a patient's medical device. The artificial intelligence may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired item location. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine-readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the implementations discussed above are described in "A survey of machine learning for big data processing" by Qiu et al. in EURASIP Journal on Advances in Signal Processing (2016) which is hereby incorporated by reference in its entirety.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method of managing one or more notifications between medical devices, comprising:
    obtaining information corresponding to a clinician at a first medical device including a first display and configured to provide a first therapy to a first patient, wherein the information includes at least a clinician identifier;
    determining whether the information satisfies coordination criteria, the coordination criteria including a device association criterion that is satisfied in accordance with a determination that the clinician identifier is associated with at least the first medical device;
    in accordance with a determination that the clinician identifier is associated with the first medical device and a second medical device including a second display and configured to provide a second therapy to a second patient thus satisfying at least one coordination criterion, detecting a first notification generated by the first medical device and a second notification generated by the second medical device, the first and second notifications being associated with one or more respective human perceivable manifestations;
    identifying, based on detecting the first and second notifications, alert information comprising medical information pertaining to a respective patient receiving medical treatment from the first medical device and the second medical device, treatment information pertaining to the medical treatment received from each device, a current location of the first medical device and a current location of the second medical device, and a current location of the clinician;
    determining, based on the identified alert information, notification priorities between the first notification and the second notification, wherein the notification priorities include a ranking of the first notification with respect to the second notification based on urgency;
    adjusting at least one human perceivable manifestation of the first notification and the second notification based on the determined notification priorities; and
    presenting one or more adjusted human perceivable manifestations of the first notification and one or more adjusted human perceivable manifestations of the second notification to a user via the first medical device, wherein the first medical device or the second medical device is an infusion pump administering a medication to the first patient or the second patient.

2. The method of claim 1, wherein the first medical device and the second medical device are located in a first patient room associated with the first patient, the method further comprising:
    detecting that the current location of the clinician is in a second patient room associated with the second patient, the second patient room being in a different geographic location than the first patient room;
    selecting, based on the determining of the notification priorities, one of the first or second notifications for display at a third medical device located in the second patient room while the clinician is in the second patient room; and
    presenting one or more respective adjusted human perceivable manifestations of the selected notification at the third medical device while the clinician is in the second patient room, wherein first notification and the second notification are not presented at the first medical device and the second medical device while the selected notification is presented at the third medical device.

3. The method of claim 2, wherein one or more human perceivable manifestations of a third notification are received at the third medical device such that the one or more human perceivable manifestations of the third notification are set for presentation by the third medical device during a period of time in which the one or more human perceivable manifestations of the first notification or the one or more human perceivable manifestations of the second notification are generated by the first medical device or the second medical device, respectively, the method further comprising:
    overriding the presentation of the one or more human perceivable manifestations of the third notification with the one or more respective adjusted human perceivable manifestations of the selected notification such that the selected notification is presented at the third medical device while the clinician is in the second patient room.

4. The method of claim 1, wherein:
the first and second medical devices are infusion pumps; and
the notification priorities between the first notification and the second notification are based, in part, on a type drug, duration of infusion, and/or time remaining for infusion.

5. The method of claim 1, wherein the notification priorities between the first notification and the second notification are based, in part, on one or more alarm types.

6. The method of claim 1, wherein the coordination criteria includes a proximity criterion that is satisfied in accordance with a determination that the current location of the first medical device and the current location of the second medical device are in proximity, and the method further comprises:
in accordance with a determination that the proximity criterion is satisfied, adjusting notification priorities between the first notification and the second notification based on the first medical device and the second medical device being in proximity to one another.

7. The method of claim 1, wherein the coordination criteria includes a remote criterion that is satisfied in accordance with a determination that the current location of the first medical device and the current location of the second medical device are remote, and the method further comprises:
in accordance with a determination that the remote criterion is satisfied, adjusting notification priorities between the first notification and the second notification based on the first medical device and the second medical device being in proximity to one another.

8. The method of claim 1, wherein the coordination criteria includes a patient association criterion that is satisfied in accordance with a determination that the first medical device and the second medical device are associated with the same patient, and the method further comprises:
in accordance with a determination that the patient association criterion is satisfied, adjusting notification priorities between the first notification and the second notification based on the first medical device and the second medical device being associated with the same patient.

9. The method of claim 8, further comprising in accordance with a determination that the patient association criterion is not satisfied, adjusting notification priorities between the first notification and the second notification based on the first medical device and the second medical device being associated with distinct patients.

10. The method of claim 1, wherein adjusting the one or more human perceivable manifestations of the first notification and the one or more human perceivable manifestations of the second notification includes adjusting visual manifestations and/or audible manifestations of the first notification and the second notification.

11. The method of claim 9, wherein adjusting audible manifestations of the first notification and the second notification includes changing a volume, pitch, rate, and/or tone of the first notification and the second notification.

12. The method of claim 9, wherein adjusting visual manifestations of the first notification and the second notification includes updating a visual color of the first notification and the second notification, or displaying a flash and/or banner for the first notification and the second notification.

13. The method of claim 1, wherein adjusting the one or more human perceivable manifestations of the first notification and the one or more human perceivable manifestations of the second notification based on the determined notification priorities includes adjusting one or more respective human perceivable manifestations notifications to emphasize higher ranked notifications over lower ranked notifications.

14. The method of claim 1, further comprising:
determining respective user response times to the adjusted one or more human perceivable manifestations of the first notification and the adjusted one or more human perceivable manifestations of the second notification;
identifying a respective adjustment to the one or more human perceivable manifestations of the first notification and the one or more human perceivable manifestations of the second notification with a lowest user response time of the respective user response times; and
adjusting subsequent human perceivable manifestations of the first notification and subsequent human perceivable manifestations of the second notification based on the determined notification priorities and adjustments to the one or more human perceivable manifestations with the lowest user response time.

15. The method of claim 1, further comprising:
detecting a third notification generated by a third medical device;
in accordance with a determination that the clinician identifier is associated with the third medical device, determining the notification priorities between the first notification, the second notification, and the third notification;
adjusting one or more respective human perceivable manifestations of the first notification, the second notification, and the third notification based on the determined notification priorities; and
presenting the one or more adjusted human perceivable manifestations of the first notification, the one or more adjusted human perceivable manifestations of the second notification, and one or more adjusted human perceivable manifestations of the third notification to the user.

16. The method of claim 1, further comprising:
detecting a fourth notification generated by the first or second medical device;
determining the notification priorities between the first notification, the second notification, and the fourth notification;
adjusting the one or more human perceivable manifestations of the first notification, the one or more human perceivable manifestations of the second notification, and one or more human perceivable manifestations of the fourth notification based on the determined notification priorities; and
presenting the one or more adjusted human perceivable manifestations of the first notification, the one or more adjusted human perceivable manifestations of the second notification, and one or more adjusted human perceivable manifestations of the fourth notification to the user.

17. A non-transitory computer readable medium storing one or more programs, the one or more programs comprising instructions, which when executed by a device, cause the device to:
obtain information corresponding to a clinician at a first medical device including a first display and configured to provide a first therapy to a first patient, wherein the information includes at least a clinician identifier;

determine whether the information satisfies coordination criteria, the coordination criteria including a device association criterion that is satisfied in accordance with a determination that the clinician identifier is associated with at least the first medical device;

in accordance with a determination that the clinician identifier is associated with the first medical device and a second medical device including a second display and configured to provide a second therapy to a second patient thus satisfying at least one coordination criterion, detect a first notification generated by the first medical device and a second notification generated by the second medical device, the first and second notifications being associated with one or more respective human perceivable manifestations;

identify, based on detecting the first and second notifications, alert information comprising medical information pertaining to a respective patient receiving a medical treatment from the first medical device and the second medical device, treatment information pertaining to the medical treatment received from each device, a current location of the first medical device and a current location of the second medical device, and a current location of the clinician;

determine, based on the identified alert information, notification priorities between the first notification and the second notification, wherein the notification priorities include a ranking of the first notification with respect to the second notification based on urgency;

adjust at least one human perceivable manifestation of the first notification and the second notification based on the determined notification priorities; and present one or more adjusted human perceivable manifestations of the first notification and one or more adjusted human perceivable manifestations of the second notification to a user via the first medical device, wherein the first medical device or the second medical device is an infusion pump administering a medication to the first patient or the second patient.

18. A computer server system for managing one or more notifications between medical devices, the computer server system comprising:

one or more processors; and memory storing one or more instructions that, when executed by the one or more processors, cause the computer server system to perform operations including:

obtaining information corresponding to a clinician at a first medical device including a first display and configured to provide a first therapy to a first patient, wherein the information includes at least a clinician identifier;

determining whether the information satisfies coordination criteria, the coordination criteria including a device association criterion that is satisfied in accordance with a determination that the clinician identifier is associated with at least the first medical device;

in accordance with a determination that the clinician identifier is associated with the first medical device and a second medical device including a second display and configured to provide a second therapy to a second patient thus satisfying at least one coordination criterion, detecting a first notification generated by the first medical device and a second notification generated by the second medical device, the first and second notifications being associated with one or more respective human perceivable manifestations;

identifying, based on detecting the first and second notifications, alert information comprising medical information pertaining to a respective patient receiving a medical treatment from the first medical device and the second medical device, treatment information pertaining to the medical treatment received from each device, a current location of the first medical device and a current location of the second medical device, and a current location of the clinician;

determining, based on the identified alert information, notification priorities between the first notification and the second notification, wherein the notification priorities include a ranking of the first notification with respect to the second notification based on urgency;

adjusting at least one human perceivable manifestation of the first notification and the second notification based on the determined notification priorities; and presenting one or more adjusted human perceivable manifestations of the first notification and one or more adjusted human perceivable manifestations of the second notification to a user via the first medical device, wherein the first medical device or the second medical device is an infusion pump administering a medication to the first patient or the second patient.

19. A method of managing one or more notifications between medical devices, comprising:

detecting a current location of a clinician, the clinician being currently associated with a first medical device located in a first patient room associated with a first patient, and a second medical device located in a second patient room associated with a second patient, the second patient room being in a different geographic location than the first patient room, wherein the first medical device includes a first display and is configured to provide a first therapy to a first patient and the second medical device includes a second display and is configured to provide a second therapy to a second patient;

detecting a first notification generated by the first medical device and a second notification generated by the second medical device, the first and second notifications being associated with one or more respective human perceivable manifestations;

identifying, based on detecting the first and second notifications, alert information comprising medical information pertaining to a respective patient receiving medical treatment from the first medical device and the second medical device, treatment information pertaining to the medical treatment received from each device, a current location of the first medical device and a current location of the second medical device, and the current location of the clinician;

determining, based on the identified alert information, notification priorities between the first notification and the second notification, wherein the notification priorities include a ranking of the first notification with respect to the second notification based on urgency;

selecting, based on the current location of the clinician in a respective patient room, one of the first medical device or the second medical device as a selected medical device, the selected medical device selected to present the first and/or second notifications;

adjusting at least one human perceivable manifestation of the first notification and the second notification based on the determined notification priorities; and presenting one or more adjusted human perceivable manifestations of the first notification and one or more adjusted human perceivable manifestations of the second notification to the clinician at the selected medical device, wherein a respective notification of a non-selected medical device is not generated by the non-selected medical device and the first medical device or the second medical device is an infusion pump administering a medication to the first patient or the second patient.

20. A non-transitory computer readable medium storing one or more programs, the one or more programs comprising instructions, which when executed by a device, cause the device to:

detect a current location of a clinician, the clinician being currently associated with a first medical device located in a first patient room associated with a first patient, and a second medical device located in a second patient room associated with a second patient, the second patient room being in a different geographic location than the first patient room, wherein the first medical device includes a first display and is configured to provide a first therapy to a first patient and the second medical device includes a second display and is configured to provide a second therapy to a second patient;

detect a first notification generated by the first medical device and a second notification generated by the second medical device, the first and second notifications being associated with one or more respective human perceivable manifestations;

identify, based on detecting the first and second notifications, alert information comprising medical information pertaining to a respective patient receiving medical treatment from the first medical device and the second medical device, treatment information pertaining to a medical treatment received from each device, a current location of the first medical device and a current location of the second medical device, and the current location of the clinician;

determine, based on the identified alert information, notification priorities between the first notification and the second notification, wherein the notification priorities include a ranking of the first notification with respect to the second notification based on urgency;

select, based on the current location of the clinician in a respective patient room, one of the first medical device or the second medical device as a selected medical device, the selected medical device selected to present the first and/or second notifications;

adjust at least one human perceivable manifestation of the first notification and the second notification based on the determined notification priorities; and present one or more adjusted human perceivable manifestations of the first notification and one or more adjusted human perceivable manifestations of the second notification to the clinician at the selected medical device, wherein a respective notification of a non-selected medical device is not generated by the non-selected medical device and the first medical device or the second medical device is an infusion pump administering a medication to the first patient or the second patient.

* * * * *